(12) United States Patent
Jansson

(10) Patent No.: US 7,592,305 B2
(45) Date of Patent: Sep. 22, 2009

(54) USE OF GHRELIN FOR TREATING MALNUTRITION IN GASTRECTOMIZED INDIVIDUALS

(75) Inventor: John-Olov Jansson, Gothenburg (SE)

(73) Assignee: Gastrotech Pharma A/S, Copenhagen K (DK)

( * ) Notice: Subject to any disclaimer, the term of this patent is extended or adjusted under 35 U.S.C. 154(b) by 0 days.

(21) Appl. No.: 10/530,866

(22) PCT Filed: Oct. 9, 2003

(86) PCT No.: PCT/DK03/00679

§ 371 (c)(1),
(2), (4) Date: Apr. 11, 2005

(87) PCT Pub. No.: WO2004/032952

PCT Pub. Date: Apr. 22, 2004

(65) Prior Publication Data

US 2006/0217296 A1    Sep. 28, 2006

(30) Foreign Application Priority Data

Oct. 10, 2002    (EP) .................................. 02022705

(51) Int. Cl.
*A61K 38/00* (2006.01)
(52) U.S. Cl. .............................. 514/2; 530/324; 530/399
(58) Field of Classification Search .................... 514/2; 530/324, 399
See application file for complete search history.

(56) References Cited

U.S. PATENT DOCUMENTS

2003/0040472 A1    2/2003    Larsen et al.

FOREIGN PATENT DOCUMENTS

| EP | 1197496 | 4/2000 |
|----|---------|--------|
| EP | 1060190 | 12/2000 |
| EP | 1 197 496 | 4/2002 |
| WO | 9723508 | 7/1997 |
| WO | 9958501 | 11/1999 |
| WO | 0026252 | 5/2000 |
| WO | 0156592 | 8/2001 |

OTHER PUBLICATIONS

Zittel T. (American Journal of Surgery 169(2), 265-70, 1995).*
Saidi F (Journal of the American College of Surgeons 189(3), 259-68, 1999).*
Liedman B. (The British Journal of Surgery 85(4), 542-7, 1998).*
Wren A. M. (The Journal of Clinical Endocrinology and Metabolism 86(12), pp. 5992-5995, 2001).*
Kojima,M. (Nature 402 (6762), 656-660, 1999).*
Hosoda,H. (J. Biol. Chem. 278(1), 64-70, 2003).*
Abstract of Taniwaka, Adv Med Sci 155(9), 623-624, 1990.*
English translation of claims 1-7 (only) of Inui, Akio, WO 02/060472, issued Aug. 8, 2002.*
Liedman et al., World J Surg 21, (1997), 416-20, "Changes in Body composition after Gastrectomy: Results of a Controlled Prospective Clinical Trial".
Fischer et al, Complications of Surgery, In: Schwartz (Ed), Principles of surgery, (1999), Seventh ed, McGraw-Hill, New York, pp. 470-472, "Postgastrectomy syndromes".
Kojima M, Hosoda H, Date Y, Nakazato M, Matsuo H, Kangawa K, Dec. 1999 Ghrelin is a growth-hormone-releasing acylated peptide from stomach. Nature 402:656-660.
Bowers CY, Momany F, Reynolds GA, Chang D, Hong A, Chang K 1980 Structure-activity relationships of a synthetic pentapeptide that specifically releases growth hormone in vitro. Endocrinology 106:663-667.
Bowers CY, Momany FA, Reynolds GA, Hong A 1984 On the in vitro and in vivo activity of a new synthetic hexapeptide that acts on the pituitary to specifically release growth hormone. Endocrinology 114:1537-1545.
Patchett AA, Nargund RP, Tata JR, Chen MH, Barakat KJ, Johnston DB, Cheng K, Chan WW, Butler B, Hickey G., Jul. 1995 Design and biological activities of L-163,191 (MK- 0677): a potent, orally active growth hormone secretagogue. Proc Natl Acad Sci U S A 92:7001-7005.
Smith RG, Cheng K, Schoen WR, Pong SS, Hickey G, Jacks T, Butler B, Chan WW, Chaung LY, Judith F., Jun. 11, 1993 A nonpeptidyl growth hormone secretagogue. Science 260:1640-1643.
Howard AD, et al., Aug. 16, 1996, A receptor in pituitary and hypothalamus that functions in growth hormone release. Science 273:974-977.
Smith RG, et al., Oct. 1997 Peptidomimetic regulation of growth hormone secretion. Endocr Rev 18:621- 645.
Asakawa et al., Gastroenterology 120 (Feb. 2001), 337-345, Ghrelin is an appetite-stimulatory signal from stomach with structural resemblance to Motilin.
Masuda et al., Biochem Biophys Res. Commun. 276 (2000), 905-908, "Ghrelin stimulates gastric acid secretion and motility in rats".
Ariyasu et al., J. Clin Endocrinol Metab 86 (Oct. 2001), 4753-4758, "Stomach is a major source of circulating ghrelin, and feeding state determines plasma ghrelin-like immunoreactivity levels in humans".
Dornonville de la Cour et al., Regul. Pept. 99 (2001), 141-150, "A-like cells in the rat stomach contain ghrelin and do not operate under gastrin control".
Ankersen et al., Drug Discovery Today, vol. 4, No. 11, Nov. 1999, 497-506, "Growth hormone secretagogues: recent advances and applications".

(Continued)

*Primary Examiner*—David Lukton
(74) *Attorney, Agent, or Firm*—Iver P. Cooper

(57) ABSTRACT

The present invention relates to use of ghrelin or an analogue thereof for the preparation of a medicament for one or more of: treatment and/or prevention of loss of body weight and body fat, prophylaxis or treatment of cachexia, stimulation of appetite, stimulation of food intake, stimulation of weight gain, or increasing body fat mass, in a gastrectomized individual.

20 Claims, 3 Drawing Sheets

OTHER PUBLICATIONS

Ariyasu et al. Delayed short-term secretory regulation of ghrelin in obese animals: Evidenced by a specific RIA for the active form of ghrelin, Endocrinology 143(9):3341-3350, Sep. 2002.

Lehto-Axtelius D., et al. Osteopenia after gastrectomy, fundectomy or antrectomy: an experimental study in the rat. Regul. Pept. 78 (1998), 41-50.

Date et al. The role of the gastric afferent vagal nerve in ghrelin-induced feeding and growth hormone secretion in rats. Gastroenterology 123 (Oct. 2002), 1120-1128.

Pinkney et al., Ghrelin gets hungry. The Lancet 359 (Apr. 20, 2002), 1360-1361.

Popovic V, et al., Low plasma ghrelin level in gastrectomized patients is accompanied by enhanced sensitivity to the ghrelin-induced growth hormone release.J Clin Endocrinol Metab. Apr. 2005;90(4):2187-91.

Dornonville de la Cour C, Lindqvist A, Egecioglu E, Tung YL, Surve V. Ohlsson C, Jansson JO, Erlanson-Albertsson C, Dickson S, Hakanson R. Ghrelin treatment reverses the reduction in weight gain and body fat in gastrectomised mice.Gut., 54:907-913, Apr. 21, 2005.

Jeon TY, Lee S, Kim HH, Kim YJ, Son HC, Kim DH, Sim MS. Changes in plasma ghrelin concentration immediately after gastrectomy in patients with early gastric cancer.J Clin Endocrinol Metab. Nov. 2004;89(11):5392-6.

le Roux CW, Neary NM, Halsey TJ, Small CJ, Martinez-Isla AM, Ghatei MA, Theodorou NA, Bloom SR. Ghrelin does not stimulate food intake in patients with surgical procedures involving vagotomy. J Clin Endocrinol Metab. May 24, 2005.

Tschop M, Smiley DL, Heiman ML. Ghrelin induces adiposity in rodents. Nature. Oct. 19, 2000;407(6806):908-12.

Wren AM, Small CJ, Ward HL, Murphy KG, Dakin CL, Taheri S, Kennedy AR, Roberts GH, Morgan DG, Ghatei MA, Bloom SR. The novel hypothalamic peptide ghrelin stimulates food intake and growth hormone secretion. Endocrinology. Nov. 2000;141(11):4325-8.

Pinkney, et al., "Ghrelin gets hungry", The Lancet, vol. 359, issue 9315, pp. 1360-1361, Apr. 20, 2002.

Partial translation, only of p. 204, paragraph 347, of Takaya, et al., "Chrelin secretion and the function thereof in human", The Journal of Japan Endocrine Society, vol. 90 extra edition, Feb. 20, 2001.

* cited by examiner

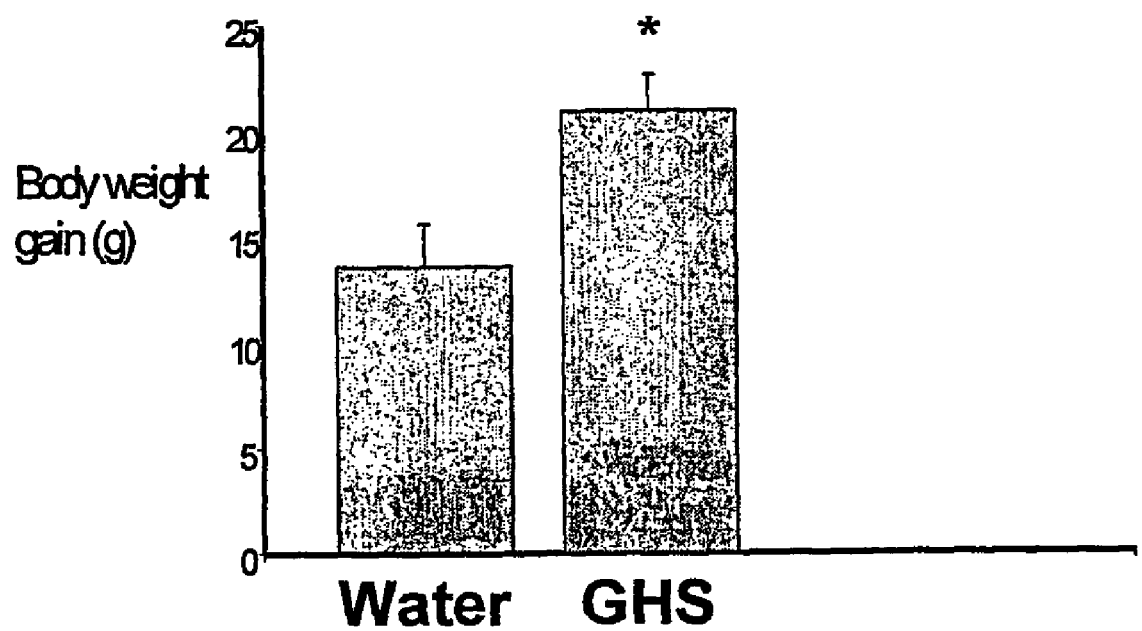

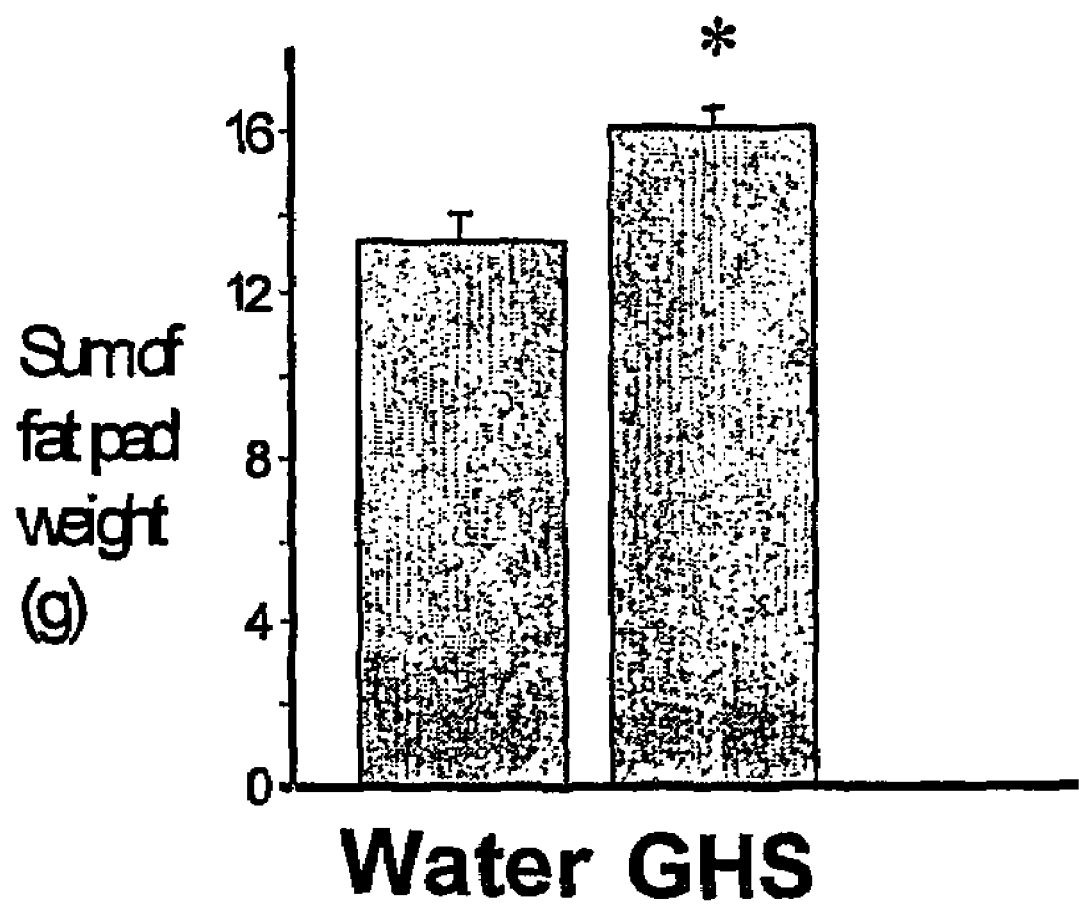

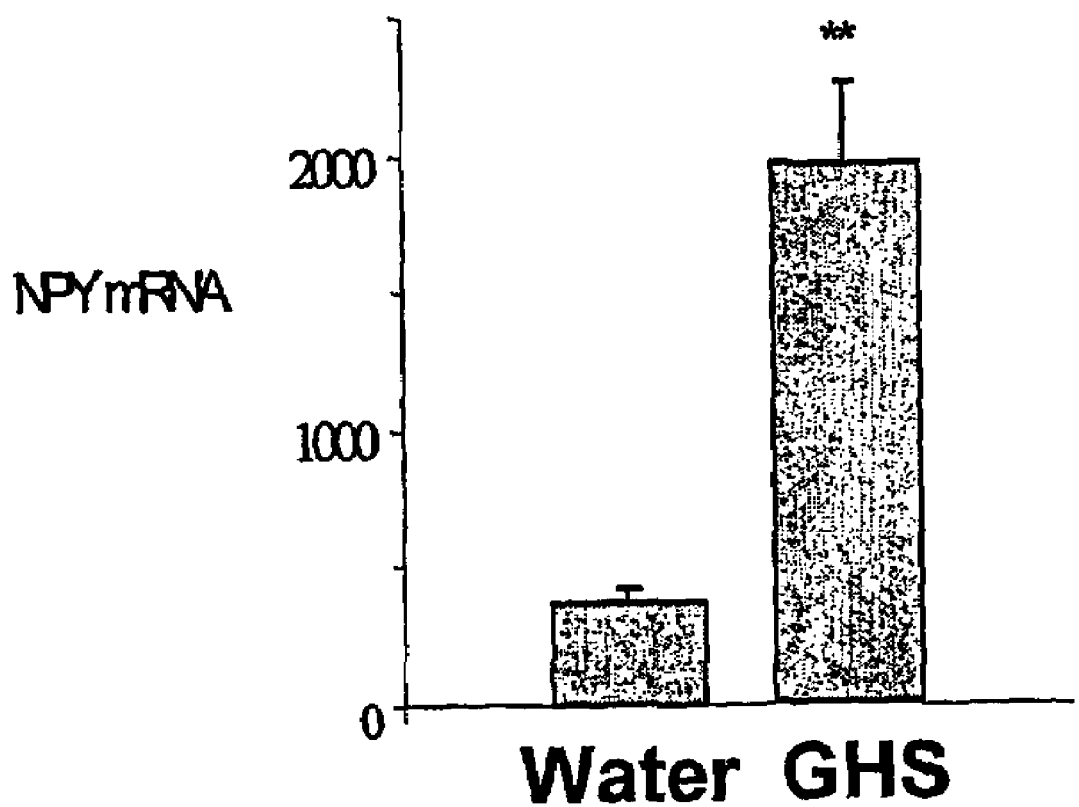

USE OF GHRELIN FOR TREATING MALNUTRITION IN GASTRECTOMIZED INDIVIDUALS

This application is a 371 of PCT/DK03/00679, filed Oct. 9, 2003, which claims foreign priority to 02022705.4, filed Oct. 10, 2002.

All patent and non-patent references cited in the present application, are hereby incorporated by reference in their entirety.

FIELD OF INVENTION

The present invention relates to the use of ghrelin or analogues thereof for treating malnutrition in an individual having been subjected to gastrectomy. Specifically, the instant invention pertains to the use of ghrelin or analogues thereof for increasing body weight, body fat mass, appetite and well being in a gastrectomized individual.

The stomach is supposed to have several important functions such as initial storage of food digestion of food by mixing it with acid and pepsin. Thereafter, the food gradually is released at a steady rate into the small intestine. A number of patients around the world have been subjected to gastrectomy for different indications. Most of them have undergone surgery because of ventricle cancer, and a few patients because of gastric ulcer, especially after severe bleeding or rupture. A variety of different types of gastrectomy have been performed throughout the years. One type used for the treatment of gastric ulcer was antrum resection in combination with selective vagotomy. In addition, surgery according to Billroth I and II, which includes resection of the antrum, was used for the treatment of gastric ulcers. Another type of surgery used to treat ventricle cancer was complete ventricle resection with a so-called Roux-en-Y, oesophago-jejunostomi. Gastrectomy, especially complete ventricle resection with Roux-en-Y, results in section of extragastric vagal nerves, I e, complete vagotomy. At present, more than three quarters of all patients who have undergone surgery for gastric cancer, have been subjected to total gastrectomy.

Even though gastrectomy may provide a remedy for cancer or complications of gastric ulcer, it is accompanied by a variety of subsequent disorders. In these patients it has been observed that both subtotal and total gastrectomy result in a loss of body weight of about 10% within the first six months after surgery, which loss was shown to be mainly due to a loss of body fat, with body cell mass and muscle mass essentially remaining unchanged (Liedman et al., World J Surg 21, (1997), 416-20. Also loss of appetite and malabsorption has been noted which is assumed to contribute to the weight loss.

In addition, gastrectomized patients suffer from fatigue, osteoporosis and also diarrhea, which is presumed to originate from a diminished capability to absorb fat. Moreover, there is anemia that is caused by a decreased absorption of iron and lack of vitamin $B_{12}$, the latter being due to lack of an intrinsic factor, which is normally produced in the stomach.

Even though gastrectomized patients are routinely given replacement therapy with vitamin $B_{12}$, iron, and calcium, they continue to suffer from fatigue, loss of fat mass and osteoporosis (Fischer et al, Complications of Surgery, In: Schwartz (Ed) Principles of surgery, (1999), Seventh ed, McGraw-Hill, New York, pp 470-472). A possible remaining problem would be the loss of the place for initial storage and digestion of the ingested food.

Therefore, a problem of the present invention resides in alleviating the symptoms gastrectomized patients encounter after surgery, in particular to provide means to obviate the patient's deficiency to keep body weight and body fat.

This problem has been solved by providing the use of ghrelin or an analogue thereof for the preparation of a medicament for the treatment of loss of body weight and body fat in a gastrectomized individual.

BACKGROUND OF INVENTION

Ghrelin is an acylated peptide of 28 amino acids in length, which has been isolated in the stomach in humans in a specific cell type, namely in the so-called A-cells, which are mainly located in the oxyntic glands in the corpus and fundus. They contain an octanoyl ester attached to a serine residue (Kojima et al, Nature, 402, (1999), 656-660). Ghrelin and its analogues are known to be releasers of growth hormone in animals and man. These peptides act via a 7-transmembrane G-protein coupled receptor which is present both in the hypothalamus and in the pituitary (Smith et al Endocr Rev 18, (1997), 621-45).

The story of ghrelin, its receptor and synthetic compounds acting through this receptor unravelled in a unique "reverse" order. In the eighties a synthetic hexapeptide from a series of opioid-like peptides was found to be able to release growth hormone (GH) from isolated pituitary cells (Bowers C Y, Momany F, Reynolds G A, Chang D, Hong A, Chang K 1980 Structure-activity relationships of a synthetic pentapeptide that specifically releases growth hormone in vitro. Endocrinology 106:663-667). Since this action was independent of the growth hormone releasing hormone (GHRH) receptor, several pharmaceutical companies embarked upon drug discovery projects based on this hexa-peptide GH secretagogue (GHS) and its putative receptor. Several series of potent and efficient peptide as well as non-peptide GH secretagogues were consequently described in the mid nineties (Bowers C Y, Momany F A, Reynolds G A, Hong A 1984 On the in vitro and in vivo activity of a new synthetic hexapeptide that acts on the pituitary to specifically release growth hormone. Endocrinology 114:1537-1545; Patchett A A, Nargund R P, Tata J R, Chen M H, Barakat K J, Johnston D B, Cheng K, Chan W W, Butler B, Hickey G, 1995 Design and biological activities of L-163, 191 (MK-0677): a potent, orally active growth hormone secretagogue. Proc Natal Accad Sic USA 92:7001-7005; Smith R G, Cheng K, Schoen W R, Pong S S, Hickey G, Jacks T, Butler B, Chan W W, Chuan L Y, Judith F. 1993 A nonpeptidyl growth hormone secretagogue. Science 260: 1640-1643).

Several years later, the receptor through which these artificial GH secretagogues acted was eventually cloned and shown to be a member of the 7TM G protein coupled receptor family (Howard A D, Feighner S D, Cully D F, Arena J P, Liberator P A, Rosenblum C I, Hamelin M, Hreniuk D L, Palyha O C, Anderson J, Paress P S, Diaz C, Chou M, Liu K K, McKee K K, Pong S S, Chuan L Y, Elbrecht A, Dashkevicz M, Heavens R, Rigby M, Sirinathsinghji D J, Dean D C, Melillo D G, Van Der Ploeg L H, 1996 A receptor in pituitary and hypothalamus that functions in growth hormone release. Science 273:974-977; Smith R G, Van Der Ploeg L H, Howard A D, Feighner S D, Cheng K, Hickey G J, Wyvratt M J, Jr., Fisher M H, Nargund R P, Patchett A A 1997 Peptidomimetic regulation of growth hormone secretion. Endocr Rev 18:621-645) In 1999 the endogenous ligand for this receptor, the hormone ghrelin, was finally discovered (Kojima M, Hosoda H, Date Y, Nakazato M, Matsuo H, Kangawa K 1999 Ghrelin is a growth-hormone-releasing acylated peptide from stomach. Nature 402:656-660). The main site for ghrelin production is the stomach, where the peptide is found in classical endocrine cells in the gastric mucosa. Ghrelin is reported to locally act in the gastrointestinal tract, in particular the stomach, since it has been found to stimulate gastric acid production and gastrointestinal motility (Asakawa et al., Gastroenterology 120 (2001), 337-345; Masuda et al., Biochem Biophys Res. Commun. 276 (2000), 905-908).

It is known that total gastrectomy of humans reduces circulating ghrelin levels to about 30% of those in normal individuals (Ariyasu et al., J. Clin Endocrinol Metab 86 (2001), 4753-4817). In rats, the ghrelin levels in circulation were lowered to about 20% of normal after surgical removal of the acid producing rumen and fundus parts of the stomach (Dornonville de la Cour et al., Regul. Pept. 99 (2001), 141-150).

Even though ghrelin has been found to be an appetite stimulatory signal, it has been noted that this stimulatory effect is lost after vagotomy (Asakawa, supra), giving rise to the notion that for a proper action of ghrelin the presence of the stomach is required.

In contrast to the general belief, the present inventors have now found that ghrelin and its analogues are still effective in gastrectomized individuals, where potential local effects in the stomach do not operate. These findings are surprising as it has been reported that the stimulation of feeding and hypothalamic NPY expression by ghrelin analogues is dependent on intact vagal innervation (Asakawa, supra).

The present invention also embraces the use of ghrelin analogues. In the context of the present application, analogues to ghrelin are to be understood as any peptide or non-peptide compound that essentially exerts the same biological effect as ghrelin in vivo. Exemplary non-peptide ghrelin analogues are described in EP 0 869 974 and EP 1 060 190, which illustrate a number of ghrelin analogues and which documents are incorporated herein by way of reference.

According to the present invention ghrelin may be utilized as the well-known acylated 28 amino acid peptide and may be produced by chemical synthesis or recombinant techniques. Techniques for producing peptides and linking an octanoyl ester to the serine no. 3 are well within the technical person's skill. Alternatively any of the analogues mentioned in the documents referred to above may be utilized. Preferred compounds are the compounds designated as NN 703 [5-Amino-5-methylex-2-enoic acid N-methyl-N-((1R)-1-(methyl-((1R)-1-(methylcarbamoyl-2-phenylethylcarbomoyl)-2-(naphtalen-2-yl)ethyl)amide] and MK677 [sometimes also designated MKO677, cf. Drug Discovery Today, vol. 4, No. 11, November 1999, 497-506] or NNC 26-1291, or NNC 26-1187 are growth hormone secretagogues of a non-peptidyl described in WO 99/58501 and WO 00/26252, respectively, all of which documents are incorporated herein by way of reference.

In summary, the present invention provides a method for chronic treatment of body weight loss, fat mass loss etc., occurring after gastrectomy, wherein a pharmaceutically effective amount of a substance, that upon administration to a gastrectomized patient leads to an increased level of a ghrelin receptor agonist, is administered to a patient.

Preferably, the treatment comprises increasing the appetite in the individual and increasing the body fat mass of the individual, which will eventually improve the sense of well being and the quality of life in the individual.

In addition, ghrelin and/or its analogues may also be utilized in combination with another stomach derived factor, so as to improve the results observed. Exemplarily mentioned factors are pacreastatin, gastrin, histamine, resistine, prostaglandins such as prostaglandin E2 and intrinsic factor.

In addition, ghrelin and/or its analogues may be used in combination with another body weight and body fat inducing factor. Exemplarily mentioned factors are melanin-concentating hormone (MCH), MCH receptors agonists, especially MCH receptor 1 agonists, neuropeptide Y (NPY), NPY receptor 1 agonists, NPY receptor 5 agonists, and NPY receptor 2 antagonists including peptide YY (PYY) and PYY (3-36), alpha-melanocyte stimulating hormone (alpha-MSH, alpha-melanocortin), melanocortin-3 receptor (MC3R) antagonists, melanocortin-4 receptor (MC4R) antagonists, agouti-related peptide (Agrp), Agrp-agonists, cocaine- and amphetamine-regulated transcript (CART) antagonists, orexin receptor 1 and receptor 2 agonists, growth hormone (GH), GH receptor agonists, insulin-like growth factor-1 (IGF-1), and IGF-1 receptor 1 agonists Furthermore, the invention relates to a composition comprising ghrelin or an analogue thereof for treating malnutrition in an gastrectomized individual, in particular for increasing his appetite, body weight, specifically his body fat mass, and eventually his well being. For instance, a compound that can increase fat mass can be identified based on its ability to stimulate incorporation of glucose into triglycerides in fat cells in vitro.

The composition will contain the active ingredient together with a pharmaceutically acceptable carrier or diluent, which will be selected by the skilled artisan according to the route of administration. The pharmaceutical carrier or diluent employed may be a conventional solid or liquid carrier, e.g. lactose, cyclodextrin, talc, gelatin, agar, pectin, magnesium stearate, cellulose-derivatives, or syrup, olive oil, phospholipids, polyoxyethylene or simply water. Similarly, the carrier or diluent may include any sustained release material known in the art, such as glyceryl monostearate or glyceryl distearate, alone or admixed with one or more waxes. The compositions may appear in conventional forms, such as capsules, tablets, aerosols, solutions, suspensions or topical applications.

For the present indication the dosage will vary depending on the compound employed and the mode of administration. Dosage levels will vary between about 0.01 µg/kg body weight to 10 mg/kg body weight daily, preferably between about 0.01 µg/kg body weight to 1 mg/kg body weight, more preferably between 0.1 to 10 µg/kg body weight. The route of administration may be any route which effectively transports the active compound to the appropriate or desired site of action, such as oral, nasal, pulmonary, transdermal or parenteral, the oral or pulmonar route being preferred.

The objective compounds may be administered as a pharmaceutically acceptable acid addition salt or, where appropriate, as a alkali metal or alkaline earth metal or lower alkylammonium salt. Such salt forms are believed to exhibit approximately the same order of activity as the free base forms. Suitable dosages may range from about 50 mg to about 200 mg, preferably from about 20 mg to about 100 mg of the compounds of formula I admixed with a pharmaceutically acceptable carrier or diluent.

SUMMARY OF INVENTION

The present invention relates to the use of ghrelin or analogues thereof for treating the symptoms of malnutrition in an individual having been subjected to gastrectomy. Specifically, the instant invention pertains to the use of ghrelin or analogues or secretagogues thereof for increasing body weight, body fat mass, appetite and the well being in an gastrectomized individual.

DESCRIPTION OF DRAWINGS

In the figures,

FIG. 1 graphically shows that treatment of gastrectomised rats with the GH secretagogue MK677 increased body weight;

FIG. 2 graphically shows that the treated animals show a higher fat pad weight;

FIG. 3 shows that treatment of gastrectomised rats with the GH secretagogue MK677 increased NPY mRNA levels in the hypothalamus.

DEFINITIONS

Amino acid: Entity comprising an amino terminal part ($NH_2$) and a carboxy terminal part (COOH) separated by a central part comprising a carbon atom, or a chain of carbon atoms, comprising at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in Table 1 herein below. Non-natural amino acids are those not listed in Table 1. Examples of non-natural amino acids are those listed e.g. in 37 C.F.R. section 1.822(b)(4), all of which are incorporated herein by reference. Further examples of non-natural amino acids are listed herein below. Amino acid residues described herein can be in the "D" or "L" isomeric form.

TABLE 1

Natural amino acids and their respective codes.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

Appetite: Appetite in an individual is assessed by measuring the amount of food ingested and by assessing the individual's desire to eat. Appetite (i.e., hunger) is typically assessed with a short questionnaire given to individuals on a random basis several times a week. Typically, subjects rate their hunger, preoccupation with food, and desire to eat greater quantities and different types of food by answering the questions using analogue scales ranging from 1, not at all, to 5, extremely.

Amino acid residue: the term "amino acid residue" is meant to encompass amino acids, either standard amino acids, non-standard amino acids or pseudo-amino acids, which have been reacted with at least one other species, such as 2, for example 3, such as more than 3 other species. In particular amino acid residues may comprise an acyl bond in place of a free carboxyl group and/or an amine-bond and/or amide bond in place of a free amine group. Furthermore, reacted amino acids residues may comprise an ester or thioester bond in place of an amide bond BMI: The body mass index (BMI) measures an individual's height/weight ratio. It is determined by calculating weight in kilograms divided by the square of height in meters. The BMI "normal" range is 19-22.

Body fat mass: Body fat mass can be measured e.g. by the fat fold technique: In this technique, a pincer-type caliper is used to measure subcutaneous fat by determining skin fold thickness at representative sites on the body. These skin fold measurements are then used to compute body fat by either adding the scores from the various measurements and using this value as an indication of the relative degree of fatness among individuals or by using the measurements in mathematical equations that have been developed to predict percent body fat.

Cachexia: a wasting disorder, the symptoms of which comprise weight loss, wasting of muscle, loss of appetite, and general debilitation. These symptoms are often associated with chronic disease.

Concentration equivalent: A concentration equivalent is an Equivalents dosage being defined as the dosage of a ghrelin-like compound having in vitro and/or in vivo the same response as evaluated from a dosage-response curve as wild-type ghrelin.

Gastrectomy: Herein, "gastrectomy" is defined as removal, loss or reduction in size of all, or part of, the stomach of an individual. Said removal or loss is preferably surgical removal.

Gastrectomized individual: Herein, the term "gastrectomized individual" refers to a Individual who has undergone a gastrectomy, i.e. all or part of said individual's stomach has been subjected to removal, loss, or reduction in size, preferably via surgical methods.

Ghrelin: a polypeptide as described in Kojima M, Hosoda H, Date Y, Nakazato M, Matsuo H, Kangawa K 1999 Ghrelin is a growth-hormone-releasing acylated peptide from stomach. Nature 402:656-660. Human 28 aa ghrelin has the amino acid of SEQ ID NO: 1.

GHS: growth hormone secretagogue

GHS-R 1a: the receptor for GHS. GHS-R 1a is also denoted GHS 1a.

Individual: A living animal or human. In preferred embodiments, the subject is a mammal, including humans and non-human mammals such as dogs, cats, pigs, cows, sheep, goats, horses, rats, and mice. In the most preferred embodiment, the subject is a human.

Isolated: is used to describe any of the various ghrelin-like compounds, polypeptides and nucleotides disclosed herein, that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified.

"Loss of body weight": defined herein as a reduction in BMI.

"Loss of body fat": defined herein as either a reduction of an individual's overall fat mass or a reduction in the percentage of an individual's body fat.

Peptide: Plurality of covalently linked amino acid residues defining a sequence and linked by amide bonds. The term is used analogously with oligopeptide and polypeptide. The amino acids may be both natural amino acids and non-natural amino acids, including any combination thereof. The natural and/or non-natural amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Receptor A receptor is a molecule, such as a protein, glycoprotein and the like, that can specifically (non-randomly) bind to another molecule

DETAILED DESCRIPTION OF THE INVENTION

The present invention relates to ghrelin or analogues thereof for treating and/or preventing weight loss and related conditions in gastrectomised individuals. Accordingly, the present invention relates to treatment and/or prevention of loss of body weight and body fat, stimulation of weight gain, and increasing body fat mass. In particular the present invention relates to treatment and/or prevention of loss of body weight and body fat, or stimulation of weight gain, more preferably treatment and/or prevention of loss of body weight and body fat. Treatment and prevention is seen when an already arising weight loss is stopped from progressing and weight gain is initiated. This is probably due to the surprising effect of ghrelin or its analogues in gastrectomised individuals to stimulate appetite, and thereby stimulate of food intake. The present invention also relates to stimulation of appetite and stimulation of food intake, more specifically to stimulation of appetite, in gastrectomised individuals. The present invention thus relates to prophylaxis or treatment of cachexia, in gastrectomised individuals.

In another embodiment, it is envisaged that ghrelin may be used as a substance to increase the anabolic factor IGF-1, and that as a result leads to increased body weight and/or prevention of loss of body weight and body fat.

One aspect of the present invention pertains to use of ghrelin or an analogue thereof for the preparation of a medicament for the treatment of loss of body weight and body fat of a gastrectomized individual.

"Ghrelin analogue" and "ghrelin-like compound" are used interchangeably herein, and are understood to refer to any peptide or non-peptide compound that essentially exerts the same biological effect as ghrelin in vivo. Exemplary non-peptide ghrelin analogues are described in EP 0 869 974 and EP 1 060 190, which illustrate a number of ghrelin analogues and which documents are incorporated herein by way of reference.

Preferably, the ghrelin-like compound according to the present invention is a compound comprising a structure defined by formula I $Z^1$-$(X^1)_m$-$(X^2)$-$(X^3)_n$-$Z^2$, wherein $Z^1$ is an optionally present protecting group each $X^1$ is independently selected from an amino acid, wherein said amino acid is selected from naturally occurring and synthetic amino acids, $X^2$ is any amino acid selected from naturally occurring and synthetic amino acids, said amino acid being modified with a bulky hydrophobic group, preferably an acyl group, or a fatty acid, each $X^3$ is independently selected from an amino acid, wherein said amino acid is selected from naturally occurring and synthetic amino acids, wherein one or more of $X^1$ and $X^3$ optionally may be modified by a bulky hydrophobic group, preferably an acyl group, or a fatty acid, $Z^2$ is an optionally present protecting group, m is an integer in the range of from 1-10 n is 0 or an integer in the range of from 1-35.

Accordingly, the term "ghrelin-like compound" includes the naturally occurring 28 aa human ghrelin, the amino acid sequence of which is shown in SEQ ID NO: 1, as well as the naturally occurring 27 aa human ghrelin, the amino acid sequence of which is shown in SEQ ID NO: 2. Thus, the present invention relates to the use of ghrelin or a peptide homologous thereto. Ghrelin is described by Kojima in Nature (1999), vol. 402,656-660.

The present invention includes diastereomers as well as their racemic and resolved enantiomerically pure forms. Ghrelin-like compounds can contain D-amino acids, L-amino acids, alpha-amino acids, beta-amino acids, gamma-amino acids, natural amino acid and synthetic amino acids or the like or a combination thereof. Preferably, amino acids present in a ghrelin-like compound are the L-enantiomer.

The ghrelin-like compound comprises an amino acid modified with a bulky hydrophobic group. The number of amino acids N-terminally to the modified amino acid is preferably within the range of from 1-9. Accordingly, m is preferably an integer in the range of from 1-9, such as of from 1-8, such as of from 1-7, such as of from 1-6, such as of from 1-5, such as of from 1-4, such as of from 1-3, such as of from 1-2, such as 2.

It is more preferred that the number of amino acids N-terminally to the modified amino acid is low, such as of from 1-3, such as of from 1-2. Most preferably 2 amino acids are positioned N-terminal to the modified amino acid.

In a preferred embodiment $(X^1)_m$ has a Gly residue in the N-terminal part of the sequence. Accordingly, in preferred embodiment $(X^1)_m$ is selected from the sequences:

Gly, Gly-Ser, Gly-Cys, Gly-Lys, Gly-Asp, Gly-Glu, Gly-Arg, Gly-His, Gly-Asn, Gly-Gln, Gly-Thr, and Gly-Tyr.

More preferably $(X^1)_m$ is selected from, Gly-Ser, and Gly-Cys, most preferably from Gly-Ser.

In other words, in a preferred embodiment the ghrelin-like compound is selected from a compound of $Z^1$-Gly-$(X^1)_{m-1}$-$(X^2)$-$(X^3)_n$-$Z^2$,       formula II $Z^1$-Gly-Ser-$(X^2)$-$(X^3)_n$-$Z^2$,       formula III and $Z^1$-Gly-$(X^2)$-$(X^3)_n$-$Z^2$.       formula IV And more preferably the ghrelin-like compound has formula III.

As described above, $X^2$ may be any amino acid modified with a bulky hydrophobic group. In particular $X^2$ is selected from the group of modified Ser, Cys, Asp, Lys, Trp, Phe, Ile, and Leu. More preferably $X^2$ is selected from the group of modified Ser, modified Cys and modified Lys, and most preferably $X^2$ is modified Ser.

Furthermore, $(X^1)_m$-$(X^2)$ is preferably Gly-Xaa-Ser*, or Gly-Xaa-Cys*, wherein Xaa is any amino acid, more preferably $(X^1)_m$-$(X^2)$ is Gly-Ser-Ser*, or Gly-Ser-Cys*, wherein * indicates that the amino acid residue is modified with a bulky hydrophobic group.

$(X^3)_n$ preferably comprises a sequences which is a fragment of ghrelin, or a variant of a fragment of ghrelin, such as human ghrelin. Accordingly, $(X^3)_n$ preferably comprises a sequence selected from one or more of the sequences shown below:

```
Phe Leu Ser Pro Glu His Gln (SEQ ID NO:22)

Phe Leu Ser Pro Glu His (SEQ ID NO:23)

Phe Leu Ser Pro Glu (SEQ ID NO:24)

Phe Leu Ser Pro (SEQ ID NO:25)

Phe Leu Ser (SEQ ID NO:26)

Phe Leu (SEQ ID NO:27)

Phe (SEQ ID NO:28)
```

In a preferred embodiment the length of the ghrelin-like compound is substantially similar to the length of human ghrelin, i.e. 27 or 28 amino acids. Accordingly, n is preferably an integer in the range of from 1-25, such as of from 1-24, such as from 1-15, such as of from 1-10, or such as of from 10-25, such as of from 10-24, such as from 15-25, such as of from 15-24.

$(X^3)_n$ may be selected from any fragment of ghrelin, such as human ghrelin, and accordingly, $(X^3)_n$ may be selected from one or more of the sequences shown below or a homologue thereof:

```
Phe Leu Ser Pro Glu His Gln Arg Val Gln Gln Arg
Lys Glu Ser Lys Lys Pro Pro Ala Lys Leu Gln Pro
Arg (SEQ ID NO:4)

Phe Leu Ser Pro Glu His Gln Arg Val Gln Gln Arg
Lys Glu Ser Lys Lys Pro Pro Ala Lys Leu Gln
Pro (SEQ ID NO:5)

Phe Leu Ser Pro Glu His Gln Arg Val Gln Gln Arg
Lys Glu Ser Lys Lys Pro Pro Ala Lys Leu
Gln (SEQ ID NO:6)

Phe Leu Ser Pro Glu His Gln Arg Val Gln Gln Arg
Lys Glu Ser Lys Lys Pro Pro Ala Lys
Leu (SEQ ID NO:7)

Phe Leu Ser Pro Glu His Gln Arg Val Gln Gln Arg
Lys Glu Ser Lys Lys Pro Pro Ala Lys (SEQ ID NO:8)

Phe Leu Ser Pro Glu His Gln Arg Val Gln Gln Arg
Lys Glu Ser Lys Lys Pro Pro Ala (SEQ ID NO:9)

Phe Leu Ser Pro Glu His Gln Arg Val Gln Gln Arg
Lys Glu Ser Lys Lys Pro Pro (SEQ ID NO:10)

Phe Leu Ser Pro Glu His Gln Arg Val Gln Gln Arg
Lys Glu Ser Lys Lys Pro (SEQ ID NO:11)

Phe Leu Ser Pro Glu His Gln Arg Val Gln Gln Arg
Lys Glu Ser Lys Lys (SEQ ID NO:12)

Phe Leu Ser Pro Glu His Gln Arg Val Gln Gln Arg
Lys Glu Ser Lys (SEQ ID NO:13)

Phe Leu Ser Pro Glu His Gln Arg Val Gln Gln Arg
Lys Glu Ser (SEQ ID NO:14)

Phe Leu Ser Pro Glu His Gln Arg Val Gln Gln Arg
Lys Glu (SEQ ID NO:15)

Phe Leu Ser Pro Glu His Gln Arg Val Gln Gln Arg
Lys (SEQ ID NO:16)

Phe Leu Ser Pro Glu His Gln Arg Val Gln Gln
Arg (SEQ ID NO:17)

Phe Leu Ser Pro Glu His Gln Arg Val Gln
Gln (SEQ ID NO:18)

Phe Leu Ser Pro Glu His Gln Arg Val
Gln (SEQ ID NO:19)

Phe Leu Ser Pro Glu His Gln Arg Val (SEQ ID NO:20)

Phe Leu Ser Pro Glu His Gln Arg (SEQ ID NO:21)

Phe Leu Ser Pro Glu His Gln (SEQ ID NO:22)

Phe Leu Ser Pro Glu His (SEQ ID NO:23)

Phe Leu Ser Pro Glu (SEQ ID NO:24)

Phe Lea Ser Pro (SEQ ID NO:25)

Phe Leu Ser (SEQ ID NO:26)

Phe Leu (SEQ ID NO:27)

Phe (SEQ ID NO:28)
```

Or selected from

```
Phe Leu Ser Pro Glu His Gln Lys Val Gln Gln Arg
Lys Glu Ser Lys Lys Pro Pro Ala Lys Leu Gln Pro
Arg (SEQ ID NO:29)

Phe Leu Ser Pro Glu His Gln Lys Val Gln Gln Arg
Lys Glu Ser Lys Lys Pro Pro Ala Lys Leu Gln
Pro (SEQ ID NO:30)

Phe Leu Ser Pro Glu His Gln Lys Val Gln Gln Arg
Lys Glu Ser Lys Lys Pro Pro Ala Lys Leu
Gln (SEQ ID NO:31)

Phe Leu Ser Pro Glu His Gln Lys Val Gln Gln Arg
Lys Glu Ser Lys Lys Pro Pro Ala Lys
Leu (SEQ ID NO:32)

Phe Leu Ser Pro Glu His Gln Lys Val Gln Gln Arg
Lys Glu Ser Lys Lys Pro Pro Ala Lys (SEQ ID NO:33)

Phe Leu Ser Pro Glu His Gln Lys Val Gln Gln Arg
Lys Glu Ser Lys Lys Pro Pro Ala (SEQ ID NO:34)

Phe Leu Ser Pro Glu His Gln Lys Val Gln Gln Arg
Lys Glu Ser Lys Lys Pro Pro (SEQ ID NO:35)

Phe Leu Ser Pro Glu His Gln Lys Val Gln Gln Arg
Lys Glu Ser Lys Lys Pro (SEQ ID NO:36)

Phe Leu Ser Pro Glu His Gln Lys Val Gln Gln Arg
Lys Glu Ser Lys Lys (SEQ ID NO:37)

Phe Leu Ser Pro Glu His Gln Lys Val Gln Gln Arg
Lys Glu Ser Lys (SEQ ID NO:38)
```

Phe Leu Ser Pro Glu His Gln Lys Val Gln Gln Arg
Lys Glu Ser (SEQ ID NO:39)

Phe Leu Ser Pro Glu His Gln Lys Val Gln Gln Arg
Lys Glu (SEQ ID NO:40)

Phe Leu Ser Pro Glu His Gln Lys Val Gln Gln Arg
Lys (SEQ ID NO:41)

Phe Leu Ser Pro Glu His Gln Lys Val Gln Gln
Arg (SEQ ID NO:42)

Phe Leu Ser Pro Glu His Glu Lys Val Gln
Gln (SEQ ID NO:43)

Phe Leu Ser Pro Glu His Gln Lys Val
Gln (SEQ ID NO:44)

Pho Leu Ser Pro Glu His Gln Lys Val (SEQ ID NO:45)

Phe Leu Ser Pro Glu His Gln Lys (SEQ ID NO:46)

Or selected from

Phe Leu Ser Pro Glu His Gln Arg Ala Gln Gln Arg
Lys Glu Ser Lys Lys Pro Pro Ala Lys Leu Gln Pro
Arg (SEQ ID NO:47)

Phe Leu Ser Pro Glu His Gln Arg Ala Gln Gln Arg
Lys Glu Ser Lys Lys Pro Pro Ala Lys Leu Gln
Pro (SEQ ID NO:48)

Phe Leu Ser Pro Glu His Gln Arg Ala Gln Gln Arg
Lys Glu Ser Lys Lys Pro Pro Ala Lys Leu
Gln (SEQ ID NO:49)

Phe Leu Ser Pro Glu His Gln Arg Ala Gln Gln Arg
Lys Glu Ser Lys Lys Pro Pro Ala Lys
Leu (SEQ ID NO:50)

Phe Leu Ser Pro Glu His Gln Arg Ala Gln Gln Arg
Lys Glu Ser Lys Lys Pro Pro Ala
Lys (SEQ ID NO:51)

Phe Leu Ser Pro Glu His Gln Arg Ala Gln Gln Arg
Lys Glu Ser Lys Lys Pro Pro Ala (SEQ ID NO:52)

Phe Leu Ser Pro Glu His Gln Arg Ala Gln Gln Arg
Lys Glu Ser Lys Lys Pro Pro (SEQ ID NO:53)

Phe Leu Ser Pro Glu His Gln Arg Ala Gln Gln Arg
Lys Glu Ser Lys Lys Pro (SEQ ID NO:54)

Phe Leu Ser Pro Glu His Gln Arg Ala Gln Gln Arg
Lys Glu Ser Lys Lys (SEQ ID NO:55)

Phe Leu Ser Pro Glu His Gln Arg Ala Gln Gln Arg
Lys Glu Ser Lys (SEQ ID NO:56)

Phe Leu Ser Pro Glu His Gln Arg Ala Gln Gln Arg
Lys Glu Ser (SEQ ID NO:57)

Phe Leu Ser Pro Glu His Gln Arg Ala Gln Gln Arg
Lys Glu(SEQ ID NO:58)

Phe Leu Ser Pro Glu His Gln Arg Ala Gln Gln Arg
Lys (SEQ ID NO:59)

Phe Leu Ser Pro Glu His Gln Arg Ala Gln Gln
Arg (SEQ ID NO:60)

Phe Leu Ser Pro Glu His Gln Arg Ala Gln
Gln (SEQ ID NO:61)

Phe Leu Ser Pro Glu His Gln Arg Ala
Gln (SEQ ID NO:62)

Phe Leu Ser Pro Glu His Gln Arg Ala (SEQ ID NO:63)

Or selected from

Phe Leu Ser Pro Glu His Gln Lys Ala Gln Gln Arg
Lys Glu Ser Lys Lys Pro Pro Ala Lys Leu Gln Pro
Arg (SEQ ID NO:64)

Phe Leu Ser Pro Glu His Gln Lys Ala Gln Gln Arg
Lys Glu Ser Lys Lys Pro Pro Ala Lys Leu Gln
Pro (SEQ ID NO:65)

Phe Leu Ser Pro Glu His Gln Lys Ala Gln Gln Arg
Lys Glu Ser Lys Lys Pro Pro Ala Lys Leu
Gln (SEQ ID NO:66)

Phe Leu Ser Pro Glu His Gln Lys Ala Gln Gln Arg
Lys Glu Ser Lys Lys Pro Pro Ala Lys
Leu (SEQ ID NO:67)

Phe Leu Ser Pro Glu His Gln Lys Ala Gln Gln Arg
Lys Glu Ser Lys Lys Pro Pro Ala
Lys (SEQ ID NO:68)

Phe Leu Ser Pro Glu His Gln Lys Ala Gln Gln Arg
Lys Glu Ser Lys Lys Pro Pro Ala (SEQ ID NO:69)

Phe Leu Ser Pro Glu His Gln Lys Ala Gln Gln Arg
Lys Glu Ser Lys Lys Pro Pro (SEQ ID NO:70)

Phe Leu Ser Pro Glu His Gln Lys Ala Gln Gln Arg
Lys Glu Ser Lys Lys Pro (SEQ ID NO:71)

Phe Leu Ser Pro Glu His Gln Lys Ala Gln Gln Arg
Lys Glu Ser Lys Lys (SEQ ID NO:72)

Phe Leu Ser Pro Glu His Gln Lys Ala Gln Gln Arg
Lys Glu Ser Lys (SEQ ID NO:73)

Phe Leu Ser Pro Glu His Gln Lys Ala Gln Gln Arg
Lys Glu Ser (SEQ ID NO:74)

Phe Leu Ser Pro Glu His Gln Lys Ala Gln Gln Arg
Lys Glu (SEQ ID NO:75)

Phe Leu Ser Pro Glu His Gln Lys Ala Gln Gln Arg
Lys (SEQ ID NO:76)

Phe Leu Ser Pro Glu His Gln Lys Aia Gln Gln
Arg (SEQ ID NO:77)

Phe Leu Ser Pro Glu His Gln Lys Ala Gln
Gln (SEQ ID NO:78)

Phe Leu Ser Pro Glu His Gln Lys Ala
Gln (SEQ ID NO:79)

Phe Leu Ser Pro Glu His Gln Lys Ala (SEQ ID NO:80)

In another embodiment $(X^3)_n$ preferably comprises or consists of a sequence selected from the sequences Phe Leu Ser Pro Glu His Gln (SEQ ID NO:22)

Phe Leu Ser Pro Glu His (SEQ ID NO:23)

Phe Leu Ser Pro Glu (SEQ ID NO:24)

Phe Leu Ser Pro (SEQ ID NO:25)

Phe Leu Ser (SEQ ID NO:26)

Phe Leu (SEQ ID NO:27)

Phe (SEQ ID NO:28)

Functionality

The ghrelin-like compounds described herein are active at the GHS receptor. The compounds can bind to the receptor, and preferably, stimulate receptor activity.

GHS receptor activity can be measured using different techniques such as detecting a change in the intracellular conformation of the GHS receptor, in the G-protein coupled activities, and/or in the intracellular messengers.

One simple measure of the ability of a ghrelin like compound to activate the ghrelin receptor is to measure its EC50, i.e. the dose at which the compound is able to activates the signalling of the receptor to half of the maximal effect of the compound.

The ghrelin receptor can either be expressed endogenously on primary cells cultures, for example pituitary cells, or heterologously expressed on cells transfected with the ghrelin receptor. Whole cell assays or assays using membranes prepared form either of these cell types can be used depending on the type of assay.

As the ghrelin receptor is generally believed to be primarily coupled to the Gq signalling pathway, any suitable assay which monitors activity in the Gq/G11 signalling pathway can be used, for example:

1) an assay measuring the activation of Gq/G11 performed for example by measurement of GTPgS binding combined with, e.g., anti-G☐q or –11 antibody precipitation in order to increase the signal to noise ratio. This assay may also detect coupling to other G-proteins than Gq/11.
2) An assay which measure the activity of phopholipase C (PLC) one of the first down-stream effector molecules in the pathway, for example by measuring the accumulation of inositol phosphate which is one of the products of PLC.
3) More down stream in the signalling cascade is the mobilization of calcium from the intracellular stores
4) Furthermore down stream signalling molecules such as the activity of different kinds of MAP kinases (p38, jun, ect.), NF-κ-B translocation and CRE driven gene transcription may also be measured.

Alternatively binding of fluorescently tagged arrestin to the activated ghrelin receptor may also be used.

In one embodiment the binding of a compound to the receptor GHS-R 1A can be measured by the use of the assay described herein above.

A ghrelin-like compound according to the invention preferably has at least about 50%, at least about 60%, at least about 70%, at least about 80%, or at least about 90%, functional activity relative to 28 aa human ghrelin as determined using the assay described herein above, and/or an EC50 greater than about 1,000, greater than about 100, or greater than about 50, or greater than about 10. Greater refers to potency and thus indicates a lesser amount is needed to achieve binding inhibition.

In one embodiment of the invention the compound has a potency (EC50) on the GHS-R 1A of less than 500 nM. In another embodiment the compound has a potency (EC50) on the GHS-R 1A of less than 100 nM, such as less than 80 nM, for example less than 60 nM, such as less than 40 nM, for example less than 20 nM, such as less than 10 nM, for example less than 5 nM, such as less than 1 nM, for example less than 0.5 nM, such as less than 0.1 nM, for example less than 0.05 nM, such as less than 0.01 nM.

In a further embodiment the dissociation constant (Kd) of the compound is less than 500 nM. In a still further embodiment the dissociation constant (Kd) of the ligand is less than 100 nM, such as less than 80 nM, for example less than 60 nM, such as less than 40 nM, for example less than 20 nM, such as less than 10 nM, for example less than 5 nM, such as less than 1 nM, for example less than 0.5 nM, such as less than 0.1 nM, for example less than 0.05 nM, such as less than 0.01 nM.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Using a recombinantly expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7, and CHO not normally expressing the receptor by an expression vector, wherein the same cell line without the expression vector can act as a control.

Identity and Homology

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

A homologue of one or more of the sequences specified herein may vary in one or more amino acids as compared to the sequences defined, but is capable of performing the same function, i.e. a homologue may be envisaged as a functional equivalent of a predetermined sequence.

As described above a homologue of any of the predetermined sequences herein may be defined as:

i) homologues comprising an amino acid sequence capable of being recognised by an antibody, said antibody also recognising the 28 aa human ghrelin, preferably the acylated 28 aa human ghrelin, and/or
ii) homologues comprising an amino acid sequence capable of binding selectively to GHS-R 1a, and/or
iii) homolougues having a substantially similar or higher binding affinity to GHS-R 1a than the 28 aa human ghrelin, preferably the acylated 28 aa human ghrelin.

In the above examples, the 28 aa human ghrelin has the sequence shown in SEQ ID NO:1, and when acylated is acylated in position 3.

The antibodies used herein may be antibodies binding the N-terminal part of ghrelin or the C-terminal part of ghrelin, preferably the N-terminal part of ghrelin. The antibodies may be antibodies as described in Ariyasu et al. "Delayed short-term secretory regulation of ghrelin in obese animals: Evidensed by a specific RIA for the active form of ghrelin, Endocrinology 143(9):3341-3350, 2002.

Examples of homologues comprises one or more conservative amino acid substitutions including one or more conservative amino acid substitutions within the same group of predetermined amino acids, or a plurality of conservative amino acid substitutions, wherein each conservative substitution is generated by substitution within a different group of predetermined amino acids.

Homologues may thus comprise conservative substitutions independently of one another, wherein at least one glycine (Gly) of said homologue is substituted with an amino acid selected from the group of amino acids consisting of Ala, Val, Leu, and Ile, and independently thereof, homologues, wherein at least one of said alanines (Ala) of said homologue thereof is substituted with an amino acid selected from the group of amino acids consisting of Gly, Val, Leu, and Ile, and independently thereof, homologues, wherein at least one valine (Val) of said homologue thereof is substituted with an amino acid selected from the group of amino acids consisting of Gly, Ala, Leu, and Ile, and independently thereof, homologues thereof, wherein at least one of said leucines (Leu) of said homologue thereof is substituted with an amino acid selected from the group of amino acids consisting of Gly, Ala, Val, and Ile, and independently thereof, homologues thereof, wherein at least one isoleucine (Ile) of said homologues thereof is substituted with an amino acid selected from the group of amino acids consisting of Gly, Ala, Val and Leu, and independently thereof, homologues thereof wherein at least one of said aspartic acids (Asp) of said homologue thereof is substituted with an amino acid selected from the group of amino acids consisting of Glu, Asn, and Gln, and independently thereof, homologues thereof, wherein at least one of said phenylalanines (Phe) of said homologues thereof is substituted with an amino acid selected from the group of amino acids consisting of Tyr, Trp, His, Pro, and preferably selected from the group of amino acids consisting of Tyr and Trp, and independently thereof, homologues thereof, wherein at least one of said tyrosines (Tyr) of said homologues thereof is substituted with an amino acid selected from the group of amino acids consisting of Phe, Trp, His, Pro, preferably an amino acid selected from the group of amino acids consisting of Phe and Trp, and independently thereof, homologues thereof, wherein at least one of said arginines (Arg) of said fragment is substituted with an amino acid selected from the group of amino acids consisting of Lys and His, and independently thereof, homologues thereof, wherein at least one lysine (Lys) of said homologues thereof is substituted with an amino acid selected from the group of amino acids consisting of Arg and His, and independently thereof, homologues thereof, wherein at least one of said asparagines (Asn) of said homologues thereof is substituted with an amino acid selected from the group of amino acids consisting of Asp, Glu, and Gln, and independently thereof, homologues thereof, wherein at least one glutamine (Gln) of said homologues thereof is substituted with an amino acid selected from the group of amino acids consisting of Asp, Glu, and Asn, and independently thereof, homologues thereof, wherein at least one proline (Pro) of said homologues thereof is substituted with an amino acid selected from the group of amino acids consisting of Phe, Tyr, Trp, and His, and independently thereof, homologues thereof, wherein at least one of said cysteines (Cys) of said homologues thereof is substituted with an amino acid selected from the group of amino acids consisting of Asp, Glu, Lys, Arg, His, Asn, Gln, Ser, Thr, and Tyr.

Conservative substitutions may be introduced in any position of a preferred predetermined sequence. It may however also be desirable to introduce non-conservative substitutions, particularly, but not limited to, a non-conservative substitution in any one or more positions.

A non-conservative substitution leading to the formation of a functionally equivalent homologue of the sequences herein would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In a preferred embodiment the binding domain comprises a homologue having an amino acid sequence at least 60% homologous to SEQ ID NO 1.

More preferably the homology is at least 65%, such as at least 70% homologous, such as at least 75% homologous, such as at least 80% homologous, such as at least 85% homologous, such as at least 90% homologous, such as at least 95% homologous, such as at least 98% homologous to SEQ ID NO 1.

In a more preferred embodiment the percentages mentioned above relates to the identity of the sequence of a homologue as compared to SEQ ID NO 1.

Homologues to SEQ ID NO: 1 may be 27 aa human ghrelin SEQ ID NO: 2, rat ghrelin SEQ ID NO: 3. Other homologues are the variants described in EP 1197496 (Kangawa) incorporated herein by reference.

Bulky Hydrophobic Group

The bulky hydrophobic group of the ghrelin-like compound according to the invention is any bulky hydrophobic group capable of providing the des-acylated 28 aa human ghrelin with binding affinity to GHS-R 1a when the Ser residue in position 3 is modified with the bulky hydrophobic group.

When the amino acid being modified contains e.g. —OH, —SH, —NH or —NH$_2$ as a substituent group in a side chain thereof, a group formed by acylating such a substituent group is preferred. The mode of linkage may thus be selected from the group consisting of ester, ether, thioester, thioether, amide and carbamide.

For example, if the modified amino acid is serine, threonine, tyrosine or oxyproline, the amino acid has a hydroxyl group in the side chain. If the modified amino acid is cysteine, the amino acid has a mercapto group in the side chain. If the modified amino acid is lysine, arginine, histidine, tryptophan, proline oroxyproline, it has an amino group or imino group in the side chain.

The hydroxyl group, mercapto group, amino group and imino group described above may thus have been chemically modified. That is, the hydroxyl group or mercapto group may be etherized, esterified, thioetherified or thioesterified. The imino group may have been iminoetherified, iminothioetherified or alkylated. The amino group may have been amidated, thioamidated or carbamidated.

Further, the mercapto group may have been disulfidated, the imino group may have been amidated or thioamidated, and the amino group may have been alkylated or thiocarbamidated.

In a preferred embodiment the modified amino acid is Ser coupled through an ester linkage to the hydrophobic group.

The hydrophobic group may be any group with a saturated or unsaturated alkyl or acyl group containing one or more carbon atoms. In one embodiment the bulky hydrophobic group is an acyl group, including groups formed by removing a hydroxyl group from an organic carboxylic acid, organic sulfonic acid or organic phosphoric acid. The organic carboxylic acid includes e.g. fatty acids, and the number of carbon atoms thereof is preferably 1 to 35. In the organic sulfonic acid or organic phosphoric acid, the number of carbon atoms thereof is preferably 1 to 35.

Accordingly, the acyl group is preferably selected from a C1-C35 acyl group, such as a C1- C20 acyl group, such as a C1-C15 acyl group, such as a C6-C15 acyl group, such as a C6-C12 acyl group, such as a C8-C12 acyl group.

More preferably the acyl group is selected from the group of C7 acyl group, C8 acyl group, C9 acyl group, C10 acyl group, C11 acyl group, and C12 acyl group. Such acyl group may be formed from octanoic acid (preferably caprylic acid), decanoic acid (preferably capric acid), or dodecanoic acid (preferably lauric acid), as well as monoene or polyene fatty acids thereof.

In one embodiment the acyl group is selected from the group of C8 acyl group, and C10 acyl group. Such acyl groups may be formed from octanoic acid (preferably caprylic acid), or decanoic acid (preferably capric acid).

In another embodiment the acyl group is selected from the group of C7 acyl group, C9 acyl group, and C11 acyl group, such as from the group of C9 acyl group and C11 acyl group.

Furthermore, the modified amino acid may be any amino acid wherein a group is modified as described in EP 1 197 496 (Kangawa), which is hereby incorporated by reference.

Protecting Group

The ghrelin-like compound according to the invention may comprise a protecting group at the N-terminus or the C-terminus or at both.

A protecting group covalently joined to the N-terminal amino group reduces the reactivity of the amino terminus under in vivo conditions. Amino protecting groups include —C1-10 alkyl, —C1-10 substituted alkyl, —C2-10 alkenyl, —C2-10 substituted alkenyl, aryl, —C1-6 alkyl aryl, —C(O)—(CH2) 1-6-COOH, —C(O)—C1-6 alkyl, —C(O)-aryl, —C (O)—O—C1-6 alkyl, or —C (O)—O-aryl. Preferably, the amino terminus protecting group is acetyl, propyl, succinyl, benzyl, benzyloxycarbonyl or tbutyloxycarbonyl.

A protecting group covalently joined to the C-terminal carboxy group reduces the reactivity of the carboxy terminus under in vivo conditions. The carboxy terminus protecting group is preferably attached to the a-carbonyl group of the last amino acid. Carboxy terminus protecting groups include amide, methylamide, and ethylamide.

Conjugates

The ghrelin-like compound may also be administered in a form, wherein the ghrelin-like compound is conjugated to another entity, in order for example, to prolong its half-life.

In one embodiment the conjugate is a conjugate of ghrelin or a derivative or homologue thereof and Ac-RYY(RK)(WI)RK)—NH$_2$, where the brackets show allowable variation of amino acid residues. Examples of peptides in the conjugate may also be found in U.S. patent application Ser. No. 2003040472

Medicament—treated Indications

In one aspect of the present invention ghrelin or an analogue thereof is used for the preparation of a medicament for use by an individual in need of such treatment. Preferably, said medicament is used to treat loss of body weight and/or body fat in of a gastrectomized individual. In another preferred embodiment, the treatment stimulates appetite and/or prevents malnutrition of the individual. "The term "malnutrition" refers to a state whereby an individual does not consume, absorb, or maintain in their body sufficient levels of one or more macro- or micro-nutrients so as to remain fit and healthy. In another, equally preferred embodiment, the treatment comprises improving the sense of well being and the quality of life in a gastrectomized individual.

In any of the treatments described herein, ghrelin or an analogue thereof may be used in combination with one or more other stomach-derived factor. This other stomach-derived factor may include any hormone, acylated or nonacylated peptide, amino acid derivative, nucleotide, fatty acid derivative, carbohydrate or other substance derived or secreted from the stomach, and may preferably (but not exclusively) be selected from the following list:

Pacreastatin, gastrin, histamine, resistine, prostaglandins such as prostaglandin E2, intrinsic factor.

In addition to "stomach derived factors", ghrelin can also be used in combination with any synthetic low or high molecular weight agonist acting on the same receptor as a "stomach derived factor".

Pharmaceutical Compositions

Whilst it is possible for the compounds or salts of the present invention to be administered as the raw chemical, it is preferred to present them in the form of a pharmaceutical composition. Accordingly, the present invention further provides a pharmaceutical composition, for medicinal application, which comprises ghrelin or an analogue or pharmaceutically acceptable salt thereof, as herein defined, and a pharmaceutically acceptable carrier therefor. Said compositions of the present invention may preferably be delivered to an individual in any way so as to achieve a beneficial effect, preferably by stimulating appetite and/or preventing malnutrition, and/or improving the individual's sense of well-being or quality of life. In one preferred embodiment, a composition according to the present invention is administered via an oral, nasal, pulmonary, transdermal or parenteral route. More preferably, the composition is administered via the oral or pulmonary route. Other drug-administration methods, which are effective to deliver the drug to a target site or to introduce the drug into the bloodstream, are also contemplated.

The compounds according to the invention may be administered with at least one other compound. The compounds may be administered simultaneously, either as separate compositions or combined in a unit dosage form, or administered sequentially.

In a preferred embodiment, the pharmaceutical composition is not immunogenic when administered to a individual for therapeutic purposes, unless that purpose is to induce an immune response.

Preferably, the composition comprises ghrelin or an analogue or pharmaceutically acceptable salt thereof and pharmaceutically acceptable carriers, vehicles and/or excipients and/or transport molecules for the treatment of loss of body weight and body fat in a gastrectomized individual.

Transport molecules act by having incorporated into or anchored to it the compound according to the invention. Any suitable transport molecules known to the skilled person may be used. Examples of transport molecules may be liposomes, micelles, and/or microspheres.

A variety of methods are available for preparing liposomes, as described in, e.g., Szoka et al., Ann. Rev. Biophys. Bioeng. 9:467 (1980), U.S. Pat. Nos. 4, 235,871, 4,501,728 and 4,837, 028, all of which are incorporated herein by reference.

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interfaces become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated nonionic detergents, the polyoxyethene moieties are oriented outward and permeated by water. This arrangement is energetically favorable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. If the surfactant concentration is increased beyond a few percent and if electrolytes are added (in the case of ionic surfactants) or the temperature is raised (in the case of nonionic surfactants), the micelles increase in size. Under these conditions, the micelles are too large to remain spherical and become ellipsoidal, cylindrical or finally lamellar in shape.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80, PLURONIC F-68, n-octyl-.beta.-D-glucopyranoside, and the like. In addition, phospholipids, such as those described for use in the production of liposomes, may also be used for micelle formation.

As used herein, the terms "pharmaceutically acceptable", "physiologically tolerable" and grammatical variations thereof, as they refer to compositions, carriers, diluents and reagents, are used interchangeably and represent that the materials are capable of administration to or upon an individual without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The pharmaceutical composition of the present invention can include pharmaceutically acceptable salts of the compounds therein. Pharmaceutically acceptable salts include the acid addition salts (formed with the free amino groups of the polypeptide).

Such salts include pharmaceutically acceptable acid addition salts, pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydriodic, phosphoric, sulpfuric and nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, ethylenediaminetetraacetic (EDTA), p-aminobenzoic, glutamic, benzenesulfonic and ptoluenesulfonic acids and the like. Further examples of pharmaceutically acceptable inorganic or organic acid addition salts include the pharmaceutical acceptable salts listed in J. Pharm. Sci. 1977, 66,2, which is incorporated herein by reference. Examples of metal salts include lithium, sodium, potassium and magnesium salts and the like.

Examples of ammonium and alkylated ammonium salts include ammonium, methylammonium, dimethylammonium, trimethylammonium, ethylammonium, hydroxyethylammonium, diethylammonium, butylammonium and tetramethylammonium salts and the like.

Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Also included within the scope of compounds or pharmaceutical acceptable acid addition salts thereof in the context of the present invention are any hydrates (hydrated forms) thereof.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

The pharmaceutical compositions formed by combining the compounds of the invention and the pharmaceutical acceptable carriers are then readily administered in a variety of dosage forms suitable for the disclosed routes of administration. The compositions may conveniently be presented in unit dosage form by methods known in the art of pharmacy.

In a preferred embodiment of the invention the composition comprises the ghrelin-like compound or a salt thereof as a lyophilisate and the composition further comprises a solvent. In another embodiment the composition is a solution of the ghrelin-like compound or a salt thereof. Preferably, the solvent may be any suitable solvents, such as described herein, and preferably the solvent is saline or a physiological buffer like phosphate buffer.

The invention also relates to a method for preparing a medicament or pharmaceutical composition comprising an compound of the invention, comprising admixing at least one ghrelin-like compound as defined above with a physiologically acceptable carrier.

In a still further aspect, the invention relates to a pharmaceutical composition comprising, as an active ingredient, a compound as defined above or a pharmaceutical acceptable salt thereof together with a pharmaceutical acceptable carrier.

Accordingly, the composition may further include the transport molecules as described above.

In a further aspect of the invention the present compounds may be administered in combination with further pharmacologically active substances known to increase body weight, e.g. melanin-concentrating hormone (MCH), MCH receptors agonists, especially MCH receptor 1 agonists, neuropeptide Y (NPY), NPY receptor 1 agonists and NPY receptor 5 agonists, NPY receptor 2 antagonists including pepetide YY (PYY) and PYY (3-36), alpha-melanocyte stimulating hormone (alpha-MSH, alpha-melanocortin), melanocortin-3 receptor (MC3R) antagonists, melanocortin-4 receptor (MC4R) antagonists, agouti-related peptide (Agrp), Agrp-agonists, cocaine- and amphetamine-regulated transcript (CART) antagonists, orexin receptor 1 and receptor 2 agonists, growth hormone (GH), GH receptor agonists, and insulin-like growth factor-1 (IGF-1), IGF-1 receptor 1 agonists or other pharmacologically active material. Moreover, the further active substance may comprise other stomach derived factors including, but not restricted to, one or more of gastrin, pancreostatin, histamine, resistine, prostaglandins such as prostaglandin E2, intrinsic factor. The combination may be in the form of kit-in-part systems, wherein the combined active substances may be used for simultaneous, sequential or separate administration.

Compositions for Oral Administration

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the composition of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Compositions for Parenteral Administration

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water. Aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions of ghrelin or an analogue or pharmaceutically acceptable salt thereof, (and for example antigenic epitopes and protease inhibitors) can be prepared in water or saline, and optionally mixed with a nontoxic surfactant. Compositions for intravenous or intra-arterial administration may include sterile aqueous solutions that may also contain buffers, liposomes, diluents and other suitable additives.

Oils useful in parenteral compositions include petroleum, animal, vegetable, or synthetic oils. Specific examples of oils useful in such compositions include peanut, soybean, sesame, cottonseed, corn, olive, petrolatum, and mineral. Suitable fatty acids for use in parenteral compositions include oleic acid, stearic acid, and isostearic acid. Ethyl oleate and isopropyl myristate are examples of suitable fatty acid esters.

Suitable soaps for use in parenteral compositions include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral compositions typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such compositions will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral compositions can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating ghrelin or an analogue or pharmaceutically acceptable salt thereof in the required amount in the appropriate solvent with various of the other ingredients enumerated above, as required, followed by filter sterilization.

Compositions for Topical Administration

The compounds of the invention can also be delivered topically. Regions for topical administration include the skin surface and also mucous membrane tissues of the rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Compositions suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

Compositions for Administration as Suppositories

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

Compounds for Nasal Administration

The compounds of the present invention may be formulated for nasal administration. The solutions or suspensions are applied directly to the nasal cavity by conventional means, for example with a dropper, pipette or spray. The compositions may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

Compounds for Aerosol Administration

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Compositions administered by aerosols may be prepared, for example, as solutions in saline, employing benzyl alcohol or other suitable preservatives, absorption promoters to enhance bioavailability, employing fluorocarbons, and/or employing other solubilizing or dispersing agents.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Administration—dosing Regimes

The pharmaceutical preparations described herein are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. When desired, compositions can be prepared with enteric coatings adapted for sustained or controlled release administration of the active ingredient.

In one aspect of the present invention, a suitable dose of the compositions described herein is administered in pharmaceutically effective amounts to an individual in need of such treatment. Herein, "pharmaceutically effective amounts", is defined as an administration involving a total amount of each active component of the medicament or pharmaceutical composition or method that is sufficient to show a meaningful patient benefit. The term "unit dosage form" as used herein refers to physically discrete units suitable as unitary dosages for human and animal subjects, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient.

The dosage requirements will vary with the particular drug composition employed, the route of administration and the particular subject being treated. Ideally, a patient to be treated by the present method will receive a pharmaceutically effective amount of the compound in the maximum tolerated dose, generally no higher than that required before drug resistance develops Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug.

A preferred dosage of a composition employed according to the invention is in a concentration equivalent to from about 0.1 mg to about 10 mg ghrelin per kg body-weight, which is preferably administered daily. More preferably, the medicament comprises a unit dosage form of from about 5 to about 250 mg of ghrelin or an analogue thereof, more preferably from about 20 mg to about 200 mg, more preferably from about 20 mg to about 100 mg. The ghrelin-like compounds of the present invention may be administered admixed with a pharmaceutically acceptable carrier or diluent.

It should be noted that the normal ghrelin response which occurs before a meal is a short-lived surge in plasma concentrations of ghrelin and that due to the relative short half life of the peptide an i.v. injection of ghrelin will ensure that a similar short-lived peak on ghrelin concentrations can be obtained. The administration route must ensure that the non-degraded, bioactive form of the peptide will be the dominating form in the circulation, which will reach the ghrelin receptors and stimulate these. Thus, in order to obtain the maximum effect of the medicament it is preferably administered from one to three times daily, each administration being within 90 minutes of a meal, such as within 85 minutes of a meal, such as within 80 minutes of a meal, such as within 75 minutes of a meal, such as within 70 minutes of a meal, such as within 65 minutes of a meal, such as within 60 minutes of a meal, such as within 55 minutes of a meal, such as within 50 minutes of a meal, such as within 45 minutes of a meal, such as within 40 minutes of a meal, such as within 35 minutes of a meal, such as within 30 minutes of a meal, such as within 25 minutes of a meal, such as within 20 minutes of a meal, such as within 15 minutes of a meal, such as within 10 minutes of a meal, such as within 5 minutes of a meal. More preferred the medicament is administered prior to each main meal, such as administered three times daily.

For the present invention the dosage will vary depending on the compound employed and the mode of administration. Dosage levels will vary between about 0.01 µg/kg body weight to 10 mg/kg body weight daily, preferably between about 0.01 µg/kg body weight to 1 mg/kg body weight, more preferably between 0.1 to 10 µg/kg body weight. For all methods of use disclosed herein for the compounds, the daily oral dosage regimen will preferably be from about 0.01 µg to about 80 mg/kg of total body weight. The daily parenteral dosage regimen about 0.01 µg to about 80 mg/kg of total body weight. The daily topical dosage regimen will preferably be from 0.01 µg to 150 mg, administered one to four, preferably two or three times daily. The daily inhalation dosage regimen will preferably be from about 0.01 µg/kg to about 1 mg/kg per day. It will also be recognized by one of skill in the art that the optimal quantity and spacing of individual dosages of a compound or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound or a pharmaceutically acceptable salt thereof given per day for a defined number of days, can be ascertained by those skilled in the art using conventional course of treatment determination tests.

Furthermore, since the "effective level" is used as the preferred endpoint for dosing, the actual dose and schedule can vary, depending on interindividual differences in pharmacokinetics, drug distribution, and metabolism. The "effective level" can be defined, for example, as the blood or tissue level desired in the patient that corresponds to a concentration of one or more compounds according to the invention.

Methods for Production of Ghrelin

Ghrelin-like compounds can be produced using techniques well known in the art. For example, a polypeptide region of a ghrelin-like compound can be chemically or biochemically synthesized and modified. Techniques for chemical synthesis of polypeptides are well known in the art. (See e.g., Vincent in Peptide and Protein Drug Delivery, New York, N.Y., Dekker, 1990.) Examples of techniques for biochemical synthesis involving the introduction of a nucleic acid into a cell and expression of nucleic acids are provided in Ausubel, Current Protocols in Molecular Biology, John Wiley, 1987-1998, and Sambrook et al., in Molecular Cloning, A Laboratory Manual, 2 d Edition, Cold Spring Harbor Laboratory Press, 1989.

Pharmaceutical compositions containing a compound of the present invention may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications.

EXAMPLES

The following examples illustrate the invention without limiting it thereto.

Example 1

Total gastrectomy was performed and followed by end-to-end anastomosis between the esophagus and the duodenum as described in Lehto-Axtelius D., et al. Osteopenia after gastrectomy, fundectomy or antrectomy: an experimental study in the rat., Regul. Pept. 78 (1998), 41-50. The gastrectomy was accompanied by total vagotomy at the level of cardia. Sham operation was performed by opening the abdomen and moving the stomach.

In sham gastrectomised rats the ghrelin levels were 2.06±0.22 ng/ml, while they were less than the least detectable level of the assay, i e, 0.25 ng/ml after gastrectomy. From four weeks after gastrectomy the animals were administered either water or the ghrelin analogue MK-0677 by gavage once daily (4 mg/kg/day).

Food intake and body weight was measured daily and throughout the experiment. Animals treated with ghrelin showed an increased desire for food. After two weeks of treatment, the animals were decapitated and blood and tissues collected and rapidly frozen. Gonadal, mesenteric and retroperitoneal fat pads were dissected and weighed, and the sum of the weight was then calculated. Ghrelin was measured in serum using a kit purchased from Phoenix Pharmaceuticals as described (Dornonville de la Cour, supra).

Treatment of gastrectomised rats with the GH secretagogue MK677, surprisingly, increased body weight. Moreover, this treatment resulted in enhanced weight of the sum of dissected fat pad weights, and increased hypothalamic levels of neuropeptide Y (NPY) mRNA.

Example 2

Competition Binding Assays

Transfected COS-7 cells were transferred to culture plates one day after transfection at a density of $1 \times 10^5$ cells per well aiming at 5-8% binding of the radioactive ligand. Two days after transfection competition binding experiments were performed for 3 hours at 4°C using 25 pM of $^{125}$I-ghrelin (Amersham, Little Chalfont, UK). Binding assays were performed in 0.5 ml of a 50 mM Hepes buffer, pH 7.4, supplemented with 1 mM $CaCl_2$, 5 mM $MgCl_2$, and 0.1% (w/v) bovine serum albumin, 40 µg/ml bacitracin. Non-specific binding was determined as the binding in the presence of 1 µM of unlabeled ghrelin. Cells were washed twice in 0.5 ml of ice-cold buffer and 0.5-1 ml of lysis buffer (8 M Urea, 2% NP40 in 3 M acetic acid) was added and the bound radioactivity was counted. Determinations were made in duplicate.

Initial experiments showed that steady state binding was reached with the radioactive ligand under these conditions.

Example 3

Receptor Activation Assays

One simple measure of the ability of a ghrelin like compound to activate the ghrelin receptor is to measure its EC50, i.e. the dose at which the compound is able to activates the signalling of the receptor to half of the maximal effect of the compound. The ghrelin receptor can either be expressed endogenously on primary cells cultures, for example pituitary cells, or heterologously expressed on cells transfected with the ghrelin receptor. Whole cell assays or assays using membranes prepared form either of these cell types can be used depending on the type of assay.

As the ghrelin receptor is generally believed to be primarily coupled to the Gq signalling pathway, any suitable assay which monitor activity in the Gq/G11 signalling pathway can be used, for example:

1) an assay measuring the activation of Gq/G11 performed for example by measurement of GTPgS binding combined with, e.g., anti-Gq or –11 antibody precipitation in order to increase the signal to noise ratio. This assay may also detect coupling to other G-proteins than Gq/11.
2) An assay which measure the activity of phopholipase C (PLC) one of the first down-stream effector molecules in the pathway, for example by measuring the accumulation of inositol phosphate which is one of the products of PLC.
3) More down stream in the signalling cascade is the mobilization of calcium from the intracellular stores
4) Further more down stream signalling molecules such as the activity of different kinds of MAP kinases (p38, jun, ect.), NF-κ-B translocation and CRE driven gene transcription may also be measured.
5) Alternatively binding of fluorescently tagged arrestin to the activated ghrelin receptor may also be used.

Example 4

Synthetic Production of Ghrelin-like Compound

Amino acid derivatives and synthesis reagents, were obtained from commercial sources. Peptide chain extension was performed by mainly using Applied Biosystem 433A synthesizer produced by Perkin Elmer, and a protected peptide derivative-resin was constructed by the Boc or Fmoc method. The protected peptide resin obtained by the Boc method was deprotected with anhydrous hydrogen fluoride (HF) in the presence of p-cresol thereby releasing the peptide, which was then purified. The protected peptide resin obtained by the Fmoc method was deprotected with trifluoroacetic acid (TFA) or dilute TFA containing various scavengers, and the released peptide was purified. Purification was performed in reversed phase HPLC on a C4 or C18 column. The purity of the purified product was confirmed by reverse phase HPLC, and its structure was confirmed by amino acid composition analysis and mass spectrometry.

The peptide of the present invention is produced by a conventional peptide synthesis method. Specifically, synthesis of acylated or alkylated peptides is exemplified below. Further, human-derived ghrelin (which may be abbreviated hereinafter to hGhrelin) or rat-derived ghrelin (which may be abbreviated hereinafter to rGhrelin) was reacted with trypsin or chymotrypsin or both the enzymes successively to give the following ghrelin fragments: 19. Ghrelin (16-28), 20. hGhrelin (1-15), 21. rGhrelin (1-15), 23. hGhrelin (1-11), 24. rGhrelin (1-11), 25. Ghrelin (1-10), 26. Ghrelin (1-9), 27. Ghrelin (1-8), and 30. Ghrelin (1-4). Then, these fragments were isolated by analytical HPLC and measured for their activity. 41. [N-Acetyl]-Ghrelin (1-10) was prepared in a usual manner by treating Ghrelin (1-10) with N-acetylsuccinimide. Human and rat ghrelin may also be made by use of a natural material.

---

SEQUENCE LISTING

```
<160> NUMBER OF SEQ ID NOS: 80

<210> SEQ ID NO 1
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Amino acid in position 3 is modified with a
      fatty acid

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
<220> FEATURE:
<221> NAME/KEY: MOD_RES
<222> LOCATION: (3)..(3)
```

<223> OTHER INFORMATION: Amino acid in position 3 is modified with a
      fatty acid

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Rattus rattus
<220> FEATURE:
<221> NAME/KEY: MOD_RES
<222> LOCATION: (3)..(3)
<223> OTHER INFORMATION: Amino acid in position 3 is modified with a
      fatty acid

<400> SEQUENCE: 3

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 25
<212> TYPE: PRT
<213> ORGANISM: Homo sapiens

<400> SEQUENCE: 4

Phe Leu Ser Pro Glu His Gln Arg Val Gln Gln Arg Lys Glu Ser Lys
1               5                   10                  15

Lys Pro Pro Ala Lys Leu Gln Pro Arg
            20                  25

<210> SEQ ID NO 5
<211> LENGTH: 24
<212> TYPE: PRT
<213> ORGANISM: Homo sapiens

<400> SEQUENCE: 5

Phe Leu Ser Pro Glu His Gln Arg Val Gln Gln Arg Lys Glu Ser Lys
1               5                   10                  15

Lys Pro Pro Ala Lys Leu Gln Pro
            20

<210> SEQ ID NO 6
<211> LENGTH: 23
<212> TYPE: PRT
<213> ORGANISM: Homo sapiens

<400> SEQUENCE: 6

Phe Leu Ser Pro Glu His Gln Arg Val Gln Gln Arg Lys Glu Ser Lys
1               5                   10                  15

Lys Pro Pro Ala Lys Leu Gln
            20

<210> SEQ ID NO 7
<211> LENGTH: 22
<212> TYPE: PRT
<213> ORGANISM: Homo sapiens

<400> SEQUENCE: 7

```
Phe Leu Ser Pro Glu His Gln Arg Val Gln Gln Arg Lys Glu Ser Lys
1               5                   10                  15

Lys Pro Pro Ala Lys Leu
            20

<210> SEQ ID NO 8
<211> LENGTH: 21
<212> TYPE: PRT
<213> ORGANISM: Homo sapiens

<400> SEQUENCE: 8

Phe Leu Ser Pro Glu His Gln Arg Val Gln Gln Arg Lys Glu Ser Lys
1               5                   10                  15

Lys Pro Pro Ala Lys
            20

<210> SEQ ID NO 9
<211> LENGTH: 20
<212> TYPE: PRT
<213> ORGANISM: Homo sapiens

<400> SEQUENCE: 9

Phe Leu Ser Pro Glu His Gln Arg Val Gln Gln Arg Lys Glu Ser Lys
1               5                   10                  15

Lys Pro Pro Ala
            20

<210> SEQ ID NO 10
<211> LENGTH: 19
<212> TYPE: PRT
<213> ORGANISM: Homo sapiens

<400> SEQUENCE: 10

Phe Leu Ser Pro Glu His Gln Arg Val Gln Gln Arg Lys Glu Ser Lys
1               5                   10                  15

Lys Pro Pro

<210> SEQ ID NO 11
<211> LENGTH: 18
<212> TYPE: PRT
<213> ORGANISM: Homo sapiens

<400> SEQUENCE: 11

Phe Leu Ser Pro Glu His Gln Arg Val Gln Gln Arg Lys Glu Ser Lys
1               5                   10                  15

Lys Pro

<210> SEQ ID NO 12
<211> LENGTH: 17
<212> TYPE: PRT
<213> ORGANISM: Homo sapiens

<400> SEQUENCE: 12

Phe Leu Ser Pro Glu His Gln Arg Val Gln Gln Arg Lys Glu Ser Lys
1               5                   10                  15

Lys

<210> SEQ ID NO 13
<211> LENGTH: 16
<212> TYPE: PRT
<213> ORGANISM: Homo sapiens
```

```
<400> SEQUENCE: 13

Phe Leu Ser Pro Glu His Gln Arg Val Gln Gln Arg Lys Glu Ser Lys
1               5                   10                  15

<210> SEQ ID NO 14
<211> LENGTH: 15
<212> TYPE: PRT
<213> ORGANISM: Homo sapiens

<400> SEQUENCE: 14

Phe Leu Ser Pro Glu His Gln Arg Val Gln Gln Arg Lys Glu Ser
1               5                   10                  15

<210> SEQ ID NO 15
<211> LENGTH: 14
<212> TYPE: PRT
<213> ORGANISM: Homo sapiens

<400> SEQUENCE: 15

Phe Leu Ser Pro Glu His Gln Arg Val Gln Gln Arg Lys Glu
1               5                   10

<210> SEQ ID NO 16
<211> LENGTH: 13
<212> TYPE: PRT
<213> ORGANISM: Homo sapiens

<400> SEQUENCE: 16

Phe Leu Ser Pro Glu His Gln Arg Val Gln Gln Arg Lys
1               5                   10

<210> SEQ ID NO 17
<211> LENGTH: 12
<212> TYPE: PRT
<213> ORGANISM: Homo sapiens

<400> SEQUENCE: 17

Phe Leu Ser Pro Glu His Gln Arg Val Gln Gln Arg
1               5                   10

<210> SEQ ID NO 18
<211> LENGTH: 11
<212> TYPE: PRT
<213> ORGANISM: Homo sapiens

<400> SEQUENCE: 18

Phe Leu Ser Pro Glu His Gln Arg Val Gln Gln
1               5                   10

<210> SEQ ID NO 19
<211> LENGTH: 10
<212> TYPE: PRT
<213> ORGANISM: Homo sapiens

<400> SEQUENCE: 19

Phe Leu Ser Pro Glu His Gln Arg Val Gln
1               5                   10

<210> SEQ ID NO 20
<211> LENGTH: 9
<212> TYPE: PRT
<213> ORGANISM: Homo sapiens

<400> SEQUENCE: 20
```

```
Phe Leu Ser Pro Glu His Gln Arg Val
1               5

<210> SEQ ID NO 21
<211> LENGTH: 8
<212> TYPE: PRT
<213> ORGANISM: Homo sapiens

<400> SEQUENCE: 21

Phe Leu Ser Pro Glu His Gln Arg
1               5

<210> SEQ ID NO 22
<211> LENGTH: 7
<212> TYPE: PRT
<213> ORGANISM: Homo sapiens

<400> SEQUENCE: 22

Phe Leu Ser Pro Glu His Gln
1               5

<210> SEQ ID NO 23
<211> LENGTH: 6
<212> TYPE: PRT
<213> ORGANISM: Homo sapiens

<400> SEQUENCE: 23

Phe Leu Ser Pro Glu His
1               5

<210> SEQ ID NO 24
<211> LENGTH: 5
<212> TYPE: PRT
<213> ORGANISM: Homo sapiens

<400> SEQUENCE: 24

Phe Leu Ser Pro Glu
1               5

<210> SEQ ID NO 25
<211> LENGTH: 4
<212> TYPE: PRT
<213> ORGANISM: Homo sapiens

<400> SEQUENCE: 25

Phe Leu Ser Pro
1

<210> SEQ ID NO 26
<211> LENGTH: 3
<212> TYPE: PRT
<213> ORGANISM: Homo sapiens

<400> SEQUENCE: 26

Phe Leu Ser
1

<210> SEQ ID NO 27
<211> LENGTH: 2
<212> TYPE: PRT
<213> ORGANISM: Homo sapiens

<400> SEQUENCE: 27

Phe Leu
```

```
<210> SEQ ID NO 28
<211> LENGTH: 1
<212> TYPE: PRT
<213> ORGANISM: Homo sapiens

<400> SEQUENCE: 28

Phe
1

<210> SEQ ID NO 29
<211> LENGTH: 25
<212> TYPE: PRT
<213> ORGANISM: Homo sapiens

<400> SEQUENCE: 29

Phe Leu Ser Pro Glu His Gln Lys Val Gln Gln Arg Lys Glu Ser Lys
1               5                   10                  15

Lys Pro Pro Ala Lys Leu Gln Pro Arg
            20                  25

<210> SEQ ID NO 30
<211> LENGTH: 24
<212> TYPE: PRT
<213> ORGANISM: Homo sapiens

<400> SEQUENCE: 30

Phe Leu Ser Pro Glu His Gln Lys Val Gln Gln Arg Lys Glu Ser Lys
1               5                   10                  15

Lys Pro Pro Ala Lys Leu Gln Pro
            20

<210> SEQ ID NO 31
<211> LENGTH: 23
<212> TYPE: PRT
<213> ORGANISM: Homo sapiens

<400> SEQUENCE: 31

Phe Leu Ser Pro Glu His Gln Lys Val Gln Gln Arg Lys Glu Ser Lys
1               5                   10                  15

Lys Pro Pro Ala Lys Leu Gln
            20

<210> SEQ ID NO 32
<211> LENGTH: 22
<212> TYPE: PRT
<213> ORGANISM: Homo sapiens

<400> SEQUENCE: 32

Phe Leu Ser Pro Glu His Gln Lys Val Gln Gln Arg Lys Glu Ser Lys
1               5                   10                  15

Lys Pro Pro Ala Lys Leu
            20

<210> SEQ ID NO 33
<211> LENGTH: 21
<212> TYPE: PRT
<213> ORGANISM: Homo sapiens

<400> SEQUENCE: 33

Phe Leu Ser Pro Glu His Gln Lys Val Gln Gln Arg Lys Glu Ser Lys
1               5                   10                  15
```

```
Lys Pro Pro Ala Lys
            20

<210> SEQ ID NO 34
<211> LENGTH: 20
<212> TYPE: PRT
<213> ORGANISM: Homo sapiens

<400> SEQUENCE: 34

Phe Leu Ser Pro Glu His Gln Lys Val Gln Gln Arg Lys Glu Ser Lys
1               5                   10                  15

Lys Pro Pro Ala
            20

<210> SEQ ID NO 35
<211> LENGTH: 19
<212> TYPE: PRT
<213> ORGANISM: Homo sapiens

<400> SEQUENCE: 35

Phe Leu Ser Pro Glu His Gln Lys Val Gln Gln Arg Lys Glu Ser Lys
1               5                   10                  15

Lys Pro Pro

<210> SEQ ID NO 36
<211> LENGTH: 18
<212> TYPE: PRT
<213> ORGANISM: Homo sapiens

<400> SEQUENCE: 36

Phe Leu Ser Pro Glu His Gln Lys Val Gln Gln Arg Lys Glu Ser Lys
1               5                   10                  15

Lys Pro

<210> SEQ ID NO 37
<211> LENGTH: 17
<212> TYPE: PRT
<213> ORGANISM: Homo sapiens

<400> SEQUENCE: 37

Phe Leu Ser Pro Glu His Gln Lys Val Gln Gln Arg Lys Glu Ser Lys
1               5                   10                  15

Lys

<210> SEQ ID NO 38
<211> LENGTH: 16
<212> TYPE: PRT
<213> ORGANISM: Homo sapiens

<400> SEQUENCE: 38

Phe Leu Ser Pro Glu His Gln Lys Val Gln Gln Arg Lys Glu Ser Lys
1               5                   10                  15

<210> SEQ ID NO 39
<211> LENGTH: 15
<212> TYPE: PRT
<213> ORGANISM: Homo sapiens

<400> SEQUENCE: 39

Phe Leu Ser Pro Glu His Gln Lys Val Gln Gln Arg Lys Glu Ser
1               5                   10                  15
```

```
<210> SEQ ID NO 40
<211> LENGTH: 14
<212> TYPE: PRT
<213> ORGANISM: Homo sapiens

<400> SEQUENCE: 40

Phe Leu Ser Pro Glu His Gln Lys Val Gln Gln Arg Lys Glu
1               5                   10

<210> SEQ ID NO 41
<211> LENGTH: 13
<212> TYPE: PRT
<213> ORGANISM: Homo sapiens

<400> SEQUENCE: 41

Phe Leu Ser Pro Glu His Gln Lys Val Gln Gln Arg Lys
1               5                   10

<210> SEQ ID NO 42
<211> LENGTH: 12
<212> TYPE: PRT
<213> ORGANISM: Homo sapiens

<400> SEQUENCE: 42

Phe Leu Ser Pro Glu His Gln Lys Val Gln Gln Arg
1               5                   10

<210> SEQ ID NO 43
<211> LENGTH: 11
<212> TYPE: PRT
<213> ORGANISM: Homo sapiens

<400> SEQUENCE: 43

Phe Leu Ser Pro Glu His Gln Lys Val Gln Gln
1               5                   10

<210> SEQ ID NO 44
<211> LENGTH: 10
<212> TYPE: PRT
<213> ORGANISM: Homo sapiens

<400> SEQUENCE: 44

Phe Leu Ser Pro Glu His Gln Lys Val Gln
1               5                   10

<210> SEQ ID NO 45
<211> LENGTH: 9
<212> TYPE: PRT
<213> ORGANISM: Homo sapiens

<400> SEQUENCE: 45

Phe Leu Ser Pro Glu His Gln Lys Val
1               5

<210> SEQ ID NO 46
<211> LENGTH: 8
<212> TYPE: PRT
<213> ORGANISM: Homo sapiens

<400> SEQUENCE: 46

Phe Leu Ser Pro Glu His Gln Lys
1               5

<210> SEQ ID NO 47
```

```
<211> LENGTH: 25
<212> TYPE: PRT
<213> ORGANISM: Homo sapiens

<400> SEQUENCE: 47

Phe Leu Ser Pro Glu His Gln Arg Ala Gln Gln Arg Lys Glu Ser Lys
1               5                   10                  15

Lys Pro Pro Ala Lys Leu Gln Pro Arg
            20                  25

<210> SEQ ID NO 48
<211> LENGTH: 24
<212> TYPE: PRT
<213> ORGANISM: Homo sapiens

<400> SEQUENCE: 48

Phe Leu Ser Pro Glu His Gln Arg Ala Gln Gln Arg Lys Glu Ser Lys
1               5                   10                  15

Lys Pro Pro Ala Lys Leu Gln Pro
            20

<210> SEQ ID NO 49
<211> LENGTH: 23
<212> TYPE: PRT
<213> ORGANISM: Homo sapiens

<400> SEQUENCE: 49

Phe Leu Ser Pro Glu His Gln Arg Ala Gln Gln Arg Lys Glu Ser Lys
1               5                   10                  15

Lys Pro Pro Ala Lys Leu Gln
            20

<210> SEQ ID NO 50
<211> LENGTH: 22
<212> TYPE: PRT
<213> ORGANISM: Homo sapiens

<400> SEQUENCE: 50

Phe Leu Ser Pro Glu His Gln Arg Ala Gln Gln Arg Lys Glu Ser Lys
1               5                   10                  15

Lys Pro Pro Ala Lys Leu
            20

<210> SEQ ID NO 51
<211> LENGTH: 21
<212> TYPE: PRT
<213> ORGANISM: Homo sapiens

<400> SEQUENCE: 51

Phe Leu Ser Pro Glu His Gln Arg Ala Gln Gln Arg Lys Glu Ser Lys
1               5                   10                  15

Lys Pro Pro Ala Lys
            20

<210> SEQ ID NO 52
<211> LENGTH: 20
<212> TYPE: PRT
<213> ORGANISM: Homo sapiens

<400> SEQUENCE: 52

Phe Leu Ser Pro Glu His Gln Arg Ala Gln Gln Arg Lys Glu Ser Lys
1               5                   10                  15
```

```
<210> SEQ ID NO 53
<211> LENGTH: 19
<212> TYPE: PRT
<213> ORGANISM: Homo sapiens

<400> SEQUENCE: 53

Phe Leu Ser Pro Glu His Gln Arg Ala Gln Gln Arg Lys Glu Ser Lys
1               5                   10                  15

Lys Pro Pro

<210> SEQ ID NO 54
<211> LENGTH: 18
<212> TYPE: PRT
<213> ORGANISM: Homo sapiens

<400> SEQUENCE: 54

Phe Leu Ser Pro Glu His Gln Arg Ala Gln Gln Arg Lys Glu Ser Lys
1               5                   10                  15

Lys Pro

<210> SEQ ID NO 55
<211> LENGTH: 17
<212> TYPE: PRT
<213> ORGANISM: Homo sapiens

<400> SEQUENCE: 55

Phe Leu Ser Pro Glu His Gln Arg Ala Gln Gln Arg Lys Glu Ser Lys
1               5                   10                  15

Lys

<210> SEQ ID NO 56
<211> LENGTH: 16
<212> TYPE: PRT
<213> ORGANISM: Homo sapiens

<400> SEQUENCE: 56

Phe Leu Ser Pro Glu His Gln Arg Ala Gln Gln Arg Lys Glu Ser Lys
1               5                   10                  15

<210> SEQ ID NO 57
<211> LENGTH: 15
<212> TYPE: PRT
<213> ORGANISM: Homo sapiens

<400> SEQUENCE: 57

Phe Leu Ser Pro Glu His Gln Arg Ala Gln Gln Arg Lys Glu Ser
1               5                   10                  15

<210> SEQ ID NO 58
<211> LENGTH: 14
<212> TYPE: PRT
<213> ORGANISM: Homo sapiens

<400> SEQUENCE: 58

Phe Leu Ser Pro Glu His Gln Arg Ala Gln Gln Arg Lys Glu
1               5                   10

<210> SEQ ID NO 59
<211> LENGTH: 13
<212> TYPE: PRT
```

(Lys Pro Pro Ala shown at top, continuation of prior sequence, position 20)

<213> ORGANISM: Homo sapiens

<400> SEQUENCE: 59

Phe Leu Ser Pro Glu His Gln Arg Ala Gln Gln Arg Lys
1               5                   10

<210> SEQ ID NO 60
<211> LENGTH: 12
<212> TYPE: PRT
<213> ORGANISM: Homo sapiens

<400> SEQUENCE: 60

Phe Leu Ser Pro Glu His Gln Arg Ala Gln Gln Arg
1               5                   10

<210> SEQ ID NO 61
<211> LENGTH: 11
<212> TYPE: PRT
<213> ORGANISM: Homo sapiens

<400> SEQUENCE: 61

Phe Leu Ser Pro Glu His Gln Arg Ala Gln Gln
1               5                   10

<210> SEQ ID NO 62
<211> LENGTH: 10
<212> TYPE: PRT
<213> ORGANISM: Homo sapiens

<400> SEQUENCE: 62

Phe Leu Ser Pro Glu His Gln Arg Ala Gln
1               5                   10

<210> SEQ ID NO 63
<211> LENGTH: 9
<212> TYPE: PRT
<213> ORGANISM: Homo sapiens

<400> SEQUENCE: 63

Phe Leu Ser Pro Glu His Gln Arg Ala
1               5

<210> SEQ ID NO 64
<211> LENGTH: 25
<212> TYPE: PRT
<213> ORGANISM: Homo sapiens

<400> SEQUENCE: 64

Phe Leu Ser Pro Glu His Gln Lys Ala Gln Gln Arg Lys Glu Ser Lys
1               5                   10                  15

Lys Pro Pro Ala Lys Leu Gln Pro Arg
            20                  25

<210> SEQ ID NO 65
<211> LENGTH: 24
<212> TYPE: PRT
<213> ORGANISM: Homo sapiens

<400> SEQUENCE: 65

Phe Leu Ser Pro Glu His Gln Lys Ala Gln Gln Arg Lys Glu Ser Lys
1               5                   10                  15

Lys Pro Pro Ala Lys Leu Gln Pro
            20

<210> SEQ ID NO 66
<211> LENGTH: 23
<212> TYPE: PRT
<213> ORGANISM: Homo sapiens

<400> SEQUENCE: 66

Phe Leu Ser Pro Glu His Gln Lys Ala Gln Gln Arg Lys Glu Ser Lys
1               5                   10                  15

Lys Pro Pro Ala Lys Leu Gln
            20

<210> SEQ ID NO 67
<211> LENGTH: 22
<212> TYPE: PRT
<213> ORGANISM: Homo sapiens

<400> SEQUENCE: 67

Phe Leu Ser Pro Glu His Gln Lys Ala Gln Gln Arg Lys Glu Ser Lys
1               5                   10                  15

Lys Pro Pro Ala Lys Leu
            20

<210> SEQ ID NO 68
<211> LENGTH: 21
<212> TYPE: PRT
<213> ORGANISM: Homo sapiens

<400> SEQUENCE: 68

Phe Leu Ser Pro Glu His Gln Lys Ala Gln Gln Arg Lys Glu Ser Lys
1               5                   10                  15

Lys Pro Pro Ala Lys
            20

<210> SEQ ID NO 69
<211> LENGTH: 20
<212> TYPE: PRT
<213> ORGANISM: Homo sapiens

<400> SEQUENCE: 69

Phe Leu Ser Pro Glu His Gln Lys Ala Gln Gln Arg Lys Glu Ser Lys
1               5                   10                  15

Lys Pro Pro Ala
            20

<210> SEQ ID NO 70
<211> LENGTH: 19
<212> TYPE: PRT
<213> ORGANISM: Homo sapiens

<400> SEQUENCE: 70

Phe Leu Ser Pro Glu His Gln Lys Ala Gln Gln Arg Lys Glu Ser Lys
1               5                   10                  15

Lys Pro Pro

<210> SEQ ID NO 71
<211> LENGTH: 18
<212> TYPE: PRT
<213> ORGANISM: Homo sapiens

<400> SEQUENCE: 71

Phe Leu Ser Pro Glu His Gln Lys Ala Gln Gln Arg Lys Glu Ser Lys
1               5                   10                  15

Lys Pro

<210> SEQ ID NO 72
<211> LENGTH: 17
<212> TYPE: PRT
<213> ORGANISM: Homo sapiens

<400> SEQUENCE: 72

Phe Leu Ser Pro Glu His Gln Lys Ala Gln Gln Arg Lys Glu Ser Lys
1               5                   10                  15

Lys

<210> SEQ ID NO 73
<211> LENGTH: 16
<212> TYPE: PRT
<213> ORGANISM: Homo sapiens

<400> SEQUENCE: 73

Phe Leu Ser Pro Glu His Gln Lys Ala Gln Gln Arg Lys Glu Ser Lys
1               5                   10                  15

<210> SEQ ID NO 74
<211> LENGTH: 15
<212> TYPE: PRT
<213> ORGANISM: Homo sapiens

<400> SEQUENCE: 74

Phe Leu Ser Pro Glu His Gln Lys Ala Gln Gln Arg Lys Glu Ser
1               5                   10                  15

<210> SEQ ID NO 75
<211> LENGTH: 14
<212> TYPE: PRT
<213> ORGANISM: Homo sapiens

<400> SEQUENCE: 75

Phe Leu Ser Pro Glu His Gln Lys Ala Gln Gln Arg Lys Glu
1               5                   10

<210> SEQ ID NO 76
<211> LENGTH: 13
<212> TYPE: PRT
<213> ORGANISM: Homo sapiens

<400> SEQUENCE: 76

Phe Leu Ser Pro Glu His Gln Lys Ala Gln Gln Arg Lys
1               5                   10

<210> SEQ ID NO 77
<211> LENGTH: 12
<212> TYPE: PRT
<213> ORGANISM: Homo sapiens

<400> SEQUENCE: 77

Phe Leu Ser Pro Glu His Gln Lys Ala Gln Gln Arg
1               5                   10

<210> SEQ ID NO 78
<211> LENGTH: 11
<212> TYPE: PRT
<213> ORGANISM: Homo sapiens

<400> SEQUENCE: 78

```
Phe Leu Ser Pro Glu His Gln Lys Ala Gln Gln
1               5                   10

<210> SEQ ID NO 79
<211> LENGTH: 10
<212> TYPE: PRT
<213> ORGANISM: Homo sapiens

<400> SEQUENCE: 79

Phe Leu Ser Pro Glu His Gln Lys Ala Gln
1               5                   10

<210> SEQ ID NO 80
<211> LENGTH: 9
<212> TYPE: PRT
<213> ORGANISM: Homo sapiens

<400> SEQUENCE: 80

Phe Leu Ser Pro Glu His Gln Lys Ala
1               5
```

The invention claimed is:

1. A method for the treatment of loss of body weight and body fat and/or treatment of cachexia, and/or stimulation of appetite and/or stimulation of food intake and/or stimulation of weight gain and/or increasing body fat mass in a gastrectomized and vagectomized individual, comprising administering a therapeutically effective amount of ghrelin or analogue thereof, or a pharmaceutically acceptable salt thereof, to said individual.

2. The method according to claim 1, wherein the ghrelin or analogue thereof is a ghrelin-like compound or a pharmaceutically acceptable salt thereof wherein the ghrelin-like compound comprises a structure defined by formula I $Z^1$-$(X^1)$-$(X^2)$-$(X^3)_n$-$Z^2$, wherein $Z^1$ is an optionally present protecting group each $X^1$ is independently selected from an amino acid, wherein said amino acid is selected from the group consisting of naturally occurring and synthetic amino acids, $X^2$ is any amino acid selected from the group consisting of naturally occurring and synthetic occurring amino acids, said amino acid being modified with a bulky hydrophobic group, each $X^3$ is independently selected from an amino acid, wherein said amino acid is selected from the group consisting of naturally occurring and synthetic amino acids, wherein one or more of $X^1$ and $X^3$ optionally may be modified by a bulky hydrophobic group, $Z^2$ is an optionally present protecting group, m is an integer in the range of from 1-10, and/or n is 0 or an integer in the range of from 1-35.

3. The method according to claim 2, wherein m is an integer in the range of from 1-9.

4. The method according to claim 2, wherein $X^2$ is selected from the group consisting of modified Ser, modified Cys and modified Lys.

5. The method according to claim 2, wherein the ghrelin-like compound is selected from the group consisting of:

$Z^1$-Gly-$(X^1)_{m-1}$-$(X^2)$-$(X^3)_n$-$Z^2$,                formula II $Z^1$-Gly-Ser-$(X^2)$-$(X^3)_n$-$Z^2$, and                    formula III $Z^1$-Gly-$(X^2)$-$(X^3)_n$-$Z^2$.                            formula IV 6. The method according to claim 2, wherein the ghrelin-like compound is having formula III.

7. The method according to claim 2, wherein $(X^3)_n$ comprises a sequence selected from the group consisting of:

```
Phe Leu Ser Pro Glu His Gln       (SEQ ID NO: 22)

Phe Leu Ser Pro Glu His           (SEQ ID NO: 23)

Phe Leu Ser Pro Glu               (SEQ ID NO: 24)

Phe Leu Ser Pro                   (SEQ ID NO: 25)

Phe Leu Ser                       (SEQ ID NO: 26)

Phe Leu                           (SEQ ID NO: 27)

Phe                               (SEQ ID NO: 28).
```

8. The method according to claim 2, wherein n is an integer in the range of from 1-25.

9. The method according to claim 2, wherein $(X^3)_n$ is selected from the group consisting of:

```
Phe Leu Ser Pro Glu His Gln Arg Val Gln Gln Arg
Lys Glu Ser Lys Lys Pro Pro Ala Lys Leu Gln Pro
Arg (SEQ ID NO:4)

Phe Leu Ser Pro Glu His Gln Arg Val Gln Gln Arg
Lys Glu Ser Lys Lys Pro Pro Ala Lys Leu Gln
Pro (SEQ ID NO:5)

Phe Leu Ser Pro Glu His Gln Arg Val Gln Gln Arg
Lys Glu Ser Lys Lys Pro Pro Ala Lys Leu
Gln (SEQ ID NO:6)

Phe Leu Ser Pro Glu His Gln Arg Val Gln Gln Arg
Lys Glu Ser Lys Lys Pro Pro Ala Lys
Leu (SEQ ID NO:7)

Phe Leu Ser Pro Glu His Gln Arg Val Gln Gln Arg
Lys Glu Ser Lys Lys Pro Pro Ala
Lys (SEQ ID NO:8)

Phe Leu Ser Pro Glu His Gln Arg Val Gln Gln Arg
Lys Glu Ser Lys Lys Pro Pro
Ala (SEQ ID NO:9)
```

-continued

```
Phe Leu Ser Pro Glu His Gln Arg Val Gln Gln Arg
Lys Glu Ser Lys Lys Pro Pro (SEQ ID NO:10)

Phe Leu Ser Pro Glu His Gln Arg Val Gln Gln Arg
Lys Glu Ser Lys Lys Pro (SEQ ID NO:11)

Phe Leu Ser Pro Glu His Gln Arg Val Gln Gln Arg
Lys Glu Ser Lys Lys (SEQ ID NO:12)

Phe Leu Ser Pro Glu His Gln Arg Val Gln Gln Arg
Lys Glu Ser Lys (SEQ ID NO:13)

Phe Leu Ser Pro Glu His Gln Arg Val Gln Gln Arg
Lys Glu Ser (SEQ ID NO:14)

Phe Leu Ser Pro Glu His Gln Arg Val Gln Gln Arg
Lys Glu (SEQ ID NO:15)

Phe Leu Ser Pro Glu His Gln Arg Val Gln Gln Arg
Lys (SEQ ID NO:16)

Phe Leu Ser Pro Glu His Gln Arg Val Gln Gln
Arg (SEQ ID NO:17)

Phe Leu Ser Pro Glu His Gln Arg Val Gln
Gln (SEQ ID NO:18)

Phe Leu Ser Pro Glu His Gln Arg Val
Gln (SEQ ID NO:19)

Phe Leu Ser Pro Glu His Gln Arg
Val (SEQ ID NO:20)

Phe Leu Ser Pro Glu His Gln Arg (SEQ ID NO:21)

Phe Leu Ser Pro Glu His Gln (SEQ ID NO:22)

Phe Leu Ser Pro Glu His (SEQ ID NO:23)

Phe Leu Ser Pro Glu (SEQ ID NO:24)

Phe Leu Ser Pro (SEQ ID NO:25)

Phe Leu Ser (SEQ ID NO:26)

Phe Leu (SEQ ID NO:27)

Phe (SEQ ID NO:28).
```

10. The method according to claim 2, wherein the bulky hydrophobic group is selected from a C1-C35 acyl group.

11. The method according to claim 2, wherein the ghrelin-like compound or a salt thereof is provided in the form of a solution.

12. The method according to claim 11, wherein the solution is a saline solution.

13. The method according to claim 1, wherein said ghrelin or analogue thereof is administered in combination with another stomach derived factor.

14. The method according to claim 1, wherein said ghrelin or analogue thereof is administered in combination with another body weight and/or body fat inducing factor.

15. The method according to claim 1, wherein the ghrelin or analogue thereof is provided in a form suitable for oral, nasal, transdermal, pulmonary, or parenteral administration.

16. The method according to claim 1, wherein the ghrelin or analogue thereof is provided in a form suitable for subcutaneous administration.

17. The method according to claim 1, wherein the ghrelin or analogue thereof is administered in a dose of from about 0.01 µg/kg body weight to 10 mg/kg body weight daily.

18. The method according to claim 1, wherein the ghrelin or analogue thereof is administered prior to or during a meal.

19. A method of inhibiting or treating the loss of body weight or body fat, or the loss of appetite, or the development of cachexia, attributable to gastrectomization, which comprises administering a therapeutically effective amount of ghrelin or an analogue thereof, or a salt thereof, to an individual at a therapeutically effective time after gastrectomization, and in which the gastrectomization is associated with vagectomization.

20. A method of inhibiting or treating the loss of body weight or body fat, or the loss of appetite, or the development of cachexia, attributable to gastrectomization, which comprises (1) administering an effective amount of ghrelin or an analogue thereof, or a salt thereof, at an effective time prior to gastrectomization, or during gastromectization, and (2) gastrectomizing the individual, and in which the gastrectomization is associated with vagectomization.

* * * * *